(12) United States Patent  
Muhamedrahimov et al.

(10) Patent No.: US 11,727,087 B2
(45) Date of Patent: Aug. 15, 2023

(54) IDENTIFICATION OF A CONTRAST PHASE DEPICTED IN A MEDICAL IMAGE

(71) Applicant: Nano-X AI Ltd., Shefayim (IL)

(72) Inventors: Raouf Muhamedrahimov, San Francisco, CA (US); Amir Bar, Berkeley, CA (US)

(73) Assignee: Nano-X AI Ltd., Shefayim (IL)

( * ) Notice: Subject to any disclaimer, the term of this patent is extended or adjusted under 35 U.S.C. 154(b) by 267 days.

(21) Appl. No.: 17/221,860

(22) Filed: Apr. 5, 2021

(65) Prior Publication Data

US 2022/0318567 A1 Oct. 6, 2022

(51) Int. Cl.
*G06T 7/00* (2017.01)
*G06F 18/214* (2023.01)
(Continued)

(52) U.S. Cl.
CPC .......... *G06F 18/2148* (2023.01); *A61B 6/481* (2013.01); *A61B 6/484* (2013.01); *G06F 18/213* (2023.01); *G06F 18/2155* (2023.01); *G06F 18/23* (2023.01); *G06N 3/045* (2023.01); *G06N 3/08* (2013.01); *G06T 7/0012* (2013.01);
(Continued)

(58) Field of Classification Search
CPC .............. G06F 18/2148; G06F 18/213; G06F 18/2155; G06F 18/23; A61B 6/481; A61B 6/484; A61B 6/5217; A61B 6/487; A61B 6/486; A61B 6/032; G06N 3/045; G06N 3/08; G06N 3/0464; G06N 3/096; G06T 7/0012; G06T 2207/10081; G06T 2207/20081; G06T 2207/20084; G06T 2207/30004; G06T 7/20; G06V 2201/03;
(Continued)

(56) References Cited

U.S. PATENT DOCUMENTS

| | | | | |
|---|---|---|---|---|
| 2010/0166273 | A1* | 7/2010 | Wismuller | G06T 7/0012 382/131 |
| 2014/0304206 | A1* | 10/2014 | Lee | A61B 6/032 706/47 |

(Continued)

OTHER PUBLICATIONS

Adebayo et al. "Sanity Checks for Saliency Maps", ArXiv Preprint ArXiv:1810.03292v1, p. 1-27, Oct. 8, 2018.
(Continued)

*Primary Examiner* — Van D Huynh

(57) ABSTRACT

There is provided a method, comprising: accessing medical images of subjects, depicting contrast phases of contrast administered to the respective subject, accessing for a first subset of the medical images, metadata indicating a respective contrast phase, wherein a second subset of the medical images are unassociated with metadata, mapping each respective contrast phase of the contrast phases to a respective time interval indicating estimated amount of time from a start of contrast administration to time of capture of the respective medical image, creating a training dataset, by labelling images of the first subset with a label indicating the respective time interval, and including the second subset as non-labelled images, and training the ML model using the training dataset for generating an outcome of a target time interval indicating estimated amount of time from the start of contrast administration, in response to an input of a target medical image.

20 Claims, 19 Drawing Sheets

(51) Int. Cl.
*G06N 3/08* (2023.01)
*A61B 6/00* (2006.01)
*G06F 18/23* (2023.01)
*G06F 18/213* (2023.01)
*G06N 3/045* (2023.01)

(52) U.S. Cl.
CPC .............. *G06T 2207/10081* (2013.01); *G06T 2207/20081* (2013.01); *G06T 2207/20084* (2013.01); *G06T 2207/30004* (2013.01); *G06V 2201/03* (2022.01)

(58) Field of Classification Search
CPC ... G06V 10/774; G06V 10/776; G06V 10/778
USPC .......................................................... 382/131
See application file for complete search history.

(56) References Cited

U.S. PATENT DOCUMENTS

| | | | | |
|---|---|---|---|---|
| 2015/0238160 | A1* | 8/2015 | Flohr | A61B 6/032 378/8 |
| 2019/0108634 | A1* | 4/2019 | Zaharchuk | G06T 3/60 |
| 2021/0279868 | A1* | 9/2021 | Ma | G06T 7/0012 |
| 2022/0012927 | A1* | 1/2022 | Sitek | G06V 10/764 |
| 2022/0334208 | A1* | 10/2022 | Tamir | G01R 33/5601 |
| 2022/0343475 | A1* | 10/2022 | Zhang | G06T 5/50 |

OTHER PUBLICATIONS

Choi et al. "Development and Validation of a Deep Learning System for Staging Liver Fibrosis by Using Contrast Agent-Enhanced CT Images in the Liver". Radiology, 289(3): 688-697, Published Online Sep. 4, 2018.

Dercle et al. "Impact of Variability in Portal Venous Phase Acquisition Timing in Tumor Density Measurement and Treatment Response Assessment: Metastatic Colorectal Cancer as a Paradigm", JCO Clinical Cancer Informatics, 1: 1-8, Nov. 2017.

He et al. "Deep Residual Learning for Image Recognition", Proceedings of the 2016 IEEE Conference on Computer Vision and Pattern Recognition, CVPR, Las Vegas, NV, USA Jun. 27-30, 2016, p. 770-778, Jun. 27, 2016.

Joffe et al. "Batch Normalization: Accelerating Deep Network Training by Reducing Internal Covariate Shift", Proceedings of the 32nd International Conference on Machine Learning, Lille, France, Jun. 1, 2015, 37: 448-456, Jun. 1, 2015.

Ma et al. "Automated Identification of Optimal Portal Venous Phase Timing With Convolutional Neural Networks", Academic Radiology, 27(2): e10-e18, Published Online May 28, 2019.

Philbrink et al. "What Does Deep Learning See? Insights From a Classifier Trained to Predict Contrast Enhancement Phase From CT Images", American Journal of Roentgenology, AJR, 211(6): 1184-1193, Published Online Nov. 7, 2018.

Sahiner et al. "Deep Learning in Medical Imaging and Radiation Therapy", Medical Physics, 46(1): e1-e36. Published Online Nov. 20, 2018.

Simonyan et al. "Deep Inside Convolutional Networks: Visualising Image Classification Models and Saliency Maps", ArXiv Preprint ArXiv:1312.6034v1, p. 1-8, Dec. 20, 2013.

Sun et al. "Automatic Segmentation of Liver Tumors From Multiphase Contrast-Enhanced CT Images Based on FCNs", Artificial Intelligence in Medicine, 83: 58-66, Published Online Mar. 27, 2017.

Sun et al. "Fast Implementation of DeLong's Algorithm for Comparing the Areas Under Correlated Receiver Operating Characteristic Curves", IEEE Signal Processing Letters, 21(11): 1389-1393, Published Online Jul. 9, 2014.

Tang et al. "Contrast Phase Classification With a Generative Adeversarial Network", Proceedings of the SPiE Medical Imaging 2020: Image Processing, Houston, TX, USA Mar. 10, 2020, 11313: 131310-1-131310-8, Mar. 10, 2020.

* cited by examiner

| Model phase | Included phases | Approx. scan timing | Assigned regression value |
|---|---|---|---|
| Non-enhanced | All before injection | 0 sec | 0.0 |
| Arterial | Early arterial | 15–20 sec | - |
|  | Late arterial | 20–35 sec | 27.5 |
| Venous | Hepatic (portal venous) | 60–90 sec | 75.0 |
|  | Nephrogenic | 100–200 sec | - |
| Delayed | Delayed (equilibrium) | 6–10 min | 480.0 |

FIG. 10

| Input | Model | Accuracy | | |
|---|---|---|---|---|
| | | Validation (DICOM) | Test (radiologist label) | Test top 2 (radiologist labels) |
| Single slice | ResNet18 | 93.6% (92.8%, 94.2%) 4310/4607 | 92.7% (88.9%, 96.5%) 165/178 | 96.6% (93.8%, 98.9%) 172/178 |
| | Conv2D-12 | 95.0% (94.4%, 95.7%) 4378/4607 | 92.7% (88.8%, 96.0%) 165/178 | 97.2% (94.4%, 99.4%) 173/178 |
| Max. projection | ResNet18 | 92.0% (91.2%, 92.8%) 4239/4607 | 87.7% (83.7%, 93.3%) 156/178 | 97.8% (95.5%, 99.4%) 174/178 |
| | Conv2D-12 | 92.6% (91.8%, 93.3%) 4264/4607 | 91.6% (87.1%, 95.5%) 163/178 | 96.6% (93.8%, 98.9%) 172/178 |
| Volumetric | ResNet18 | 92.2% (91.4%, 93.0%) 4249/4607 | 91.6% (87.1%, 95.5%) 163/178 | 97.8% (95.5%, 99.4%) 174/178 |
| | Conv2D-12 | 92.4% (91.6%, 93.1%) 4256/4607 | 93.3% (89.3%, 96.6%) 166/178 | 98.3% (96.1%, 100%) 175/178 |

FIG. 11

Labelled: Delayed
Predicted: Venous

Labelled: Delayed
Predicted: Non-contrast

Labelled: Delayed
Predicted: Non-contrast

Labelled: Arterial
Predicted: Venous

| Chest training samples | Random weight initialization | | | | Transferred initial weights | | | |
|---|---|---|---|---|---|---|---|---|
| | Validation AUC (DICOM labels) | | Test AUC (radiologist labels) | | Validation AUC (DICOM labels) | | Test AUC (radiologist labels) | |
| 0 | 0.571 (0.531, 0.610) | | 0.453 (0.382, 0.524) | | 0.764 (0.734, 0.795) | | 0.776 (0.721, 0.832) | |
| 100 | 0.790 (0.758, 0.821) | | 0.752 (0.694, 0.810) | | 0.968 (0.954, 0.983) | | 0.999 (0.998, 1.000) | |
| 1000 | 0.978 (0.966, 0.990) | | 0.993 (0.981, 1.000) | | 0.982 (0.975, 0.990) | | 0.999 (0.997, 1.000) | |
| 9500 | 0.983 (0.973, 0.993) | | 0.994 (0.982, 1.000) | | 0.984 (0.976, 0.992) | | 0.998 (0.994, 1.000) | |

FIG. 14

IDENTIFICATION OF A CONTRAST PHASE DEPICTED IN A MEDICAL IMAGE

BACKGROUND OF THE INVENTION

The present invention, in some embodiments thereof, relates to machine learning (ML) models and, more specifically, but not exclusively, to ML models for analysis of contrast enhanced medical images.

Contrast enhanced medical images, for example, contrast CT series scans, are multiple images (e.g., CT scans) obtained during various stages of contrast administration. CT scans are usually obtained at least with and without contrast, for example, to highlight certain structures such as blood vessels that are difficult to identify without contrast, but that appear in the contrast images. Knowing the state of the contrast depicted in the image may be important for diagnosis of certain medical conditions.

SUMMARY OF THE INVENTION

According to a first aspect, a computer-implemented method of training a machine learning (ML) model for classification of contrast phases of a target medical image, comprises: accessing a plurality of medical images of a plurality of subjects, depicting a plurality of contrast phases of contrast administered to the respective subject, accessing for a first subset of the plurality of medical images, metadata indicating a respective contrast phase selected from the plurality of contrast phases, wherein a second subset of the plurality of medical images are unassociated with metadata, mapping each respective contrast phase of the plurality of contrast phases to a respective time interval indicating estimated amount of time from a start of contrast administration to time of capture of the respective medical image, creating a training dataset, by labelling images of the first subset with a label indicating the respective time interval, and including the second subset as non-labelled images, and training the ML model using the training dataset for generating an outcome of a target time interval indicating estimated amount of time from the start of contrast administration, in response to an input of a target medical image.

According to a second aspect, a computer-implemented method of automatically tagging a target medical image with an indication of a contrast phase, comprises: inputting a target medical image into an ML model trained on a training dataset of a plurality of medical images of a plurality of subjects, depicting a plurality of contrast phases of contrast administered to the respective subject, wherein a first subset of medical images having metadata indicating a respective contrast phase selected from the plurality of contrast phases are labelled with a time interval indicating estimated amount of time from a start of contrast administration mapped to the respective contrast phase, and a second subset of the plurality of medical images unassociated with metadata are unlabeled, obtaining from the ML model, an outcome of a target time interval indicating estimated amount of time from the start of contrast administration, and automatically tagging the target medical image with a tag indicating the target time interval.

According to a third aspect, a device for training a machine learning (ML) model for classification of contrast phases of a target medical image, comprises: at least one hardware processor executing a code for: accessing a plurality of medical images of a plurality of subjects, depicting a plurality of contrast phases of contrast administered to the respective subject, accessing for a first subset of the plurality of medical images, metadata indicating a respective contrast phase selected from the plurality of contrast phases, wherein a second subset of the plurality of medical images are unassociated with metadata, mapping each respective contrast phase of the plurality of contrast phases to a respective time interval indicating estimated amount of time from a start of contrast administration to time of capture of the respective medical image, creating a training dataset, by labelling images of the first subset with a label indicating the respective time interval, and including the second subset as non-labelled images, and training the ML model using the training dataset for generating an outcome of a target time interval indicating estimated amount of time from the start of contrast administration, in response to an input of a target medical image.

In a further implementation of the first, second, and third aspects, further comprising: accessing a second plurality of medical images of a second plurality of subjects, depicting the plurality of contrast phases and unassociated with metadata indicating respective contrast phases, feeding each one of the second plurality of medical images into the ML model, obtaining as the outcome of the ML model, a plurality of target time intervals for the second plurality of medical images, clustering the plurality of target time intervals for the second plurality of medical images into a plurality of clusters, mapping a first subset of the plurality of clusters to the plurality of contrast phases, wherein a second subset of the plurality of clusters is non-mapped to the plurality of contrast phases, and at least one of: (i) designating at least one new contrast phase for the second subset of the plurality of clusters, and (ii) designating a plurality of new contrast phases to replace a certain contrast phase of the plurality of contrast phases for the first subset of the plurality of clusters.

In a further implementation of the first, second, and third aspects, the plurality of contrast phases are selected from a group consisting of: not enhanced, arterial phase, venous phase, and delayed phase, wherein the at least one new contrast phase comprises a nephrogenic phase between the venous phase and delayed phase, and wherein the designating the plurality of new contrast phases to replace the certain contrast phase comprise early arterial and late arterial replacing arterial phase.

In a further implementation of the first, second, and third aspects, further comprising mapping the target time interval to one of a plurality of contrast phases including the at least one new contrast phase, and the designated plurality of new contrast phases, and automatically generating a tag indicating the mapped one of the plurality of contrast phases for the target image.

In a further implementation of the first, second, and third aspects, mapping comprises mapping a target time interval of zero to all phases before injection, mapping the target time interval of 15-20 seconds to early arterial contrast phase, mapping the target time interval of 20-35 seconds to later arterial contrast phase, mapping the target time interval of 60-90 seconds to hepatic portal venous contrast phase, mapping the target time interval of 100-200 seconds to nephrogenic contrast phase, and mapping the target time interval of 6-10 minutes to delayed contrast phase.

In a further implementation of the first, second, and third aspects, the training dataset comprises a second training dataset, and training the ML model comprises training the second ML model, and further comprising: creating a first training dataset, by labelling images of the first subset with a label indicating the respective contrast phase, and including the second subset as non-labelled images, training a first ML model using the first training dataset for generating a certain classification label indicating a certain contrast phase selected from a plurality of classification labels indicating the plurality of contrast phases, and training the second ML model on the second training dataset by using the first ML model as an initial state.

In a further implementation of the first, second, and third aspects, the metadata is used as weak labels for the first training dataset, and training the first ML model is done using semi-supervised classification training.

In a further implementation of the first, second, and third aspects, the first ML model comprises a classifier, and the second ML model comprises a regressor.

In a further implementation of the first, second, and third aspects, the first ML model and the second ML model are implemented using a common convolutional neural network (CNN) architecture, wherein the first ML model comprises an output layer with a plurality of outputs corresponding to the plurality of contrast phases and the second ML model comprises an output layer with a single output corresponding to the target time interval, wherein weights of the second ML model prior to training are initialized with weights of the trained first ML model.

In a further implementation of the first, second, and third aspects, the ML model comprises a first ML model trained on medical images depicting a first body region, and further comprising creating a second training dataset using second medical images depicting a second body region, and training a second ML model on the second training dataset using the trained first ML model as an initial state, wherein the first ML model and the second ML model share a common feature space with similarities in distribution of features associated with contrast enhancement in images depicting the first body region and images depicting the second body region.

In a further implementation of the first, second, and third aspects, the second training dataset includes less than about 100 medical images, and the first training dataset includes over about 10000 medical images.

In a further implementation of the first, second, and third aspects, the first ML model is trained on CT abdomen medical images, and the second ML model is trained on CT chest medical images, or the first ML model is trained on CT chest medical images, and the second ML model is trained on CT abdomen medical images.

In a further implementation of the first, second, and third aspects, the metadata comprises DICOM free text stored as metadata.

In a further implementation of the first, second, and third aspects, each of the plurality of medical images comprises a three (3D) dataset, and further comprising extract an input representation of the 3D dataset, wherein the training dataset includes the input representation, and a target input representation of the target medical image is fed into the trained ML model.

In a further implementation of the first, second, and third aspects, the input representation is selected from a group consisting of: a single two dimensional (2D) slice selected from a plurality of slices of the 3D dataset, a maximum intensity projection (MIP) in a selected plane computed from the 3D dataset, and a volumetric subset selected from the 3D dataset.

In a further implementation of the first, second, and third aspects, the ML model is implemented as a convolutional neural network (CNN) with 12 convolutional layers, each layer with a filter size 3×3 and stride 1, wherein after every 2 convolutions, downsampling by max-pooling is performed with kernel size 2×2 and stride 2, where the first 2 convolutional layers have 16 filters, with the number of filters doubled after each downsampling layer except for the last 2 convolutional layers, which each include 256 filters, wherein a global max-pooling layer is applied to the final feature maps and output to single output node, and wherein batch normalization (BN) is applied after each convolution before rectified linear unit activation (ReLU).

In a further implementation of the first, second, and third aspects, mapping comprises: mapping a non-enhanced contrast phase to a value of zero seconds, mapping an arterial contrast phase to a value of 27.5 seconds, mapping a venous contrast phase to a value of 75 seconds, and mapping a delayed contrast phase to a value of 480 seconds.

In a further implementation of the first, second, and third aspects, the plurality of medical images and the target medical image comprise a CT scan, and the plurality of contrast phases are based on intravenous (IV) contrast administered to the respective subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 10 is a table of general scan acquisition time delays used for obtaining different contrast phases for training a regression ML model, as part of the experiment, in accordance with some embodiments of the present invention;

FIG. 11 is a table presenting Abdomen CT contrast enhancement phase classifier performance results using the 12-layer CNN ML classifier and ResNet 18 architectures, for the experiment, in accordance with some embodiments of the present invention;

FIG. 14 is a table presenting transfer learning results, for the experiment, in accordance with some embodiments of the present invention;

DESCRIPTION OF SPECIFIC EMBODIMENTS OF THE INVENTION

Figure 1:
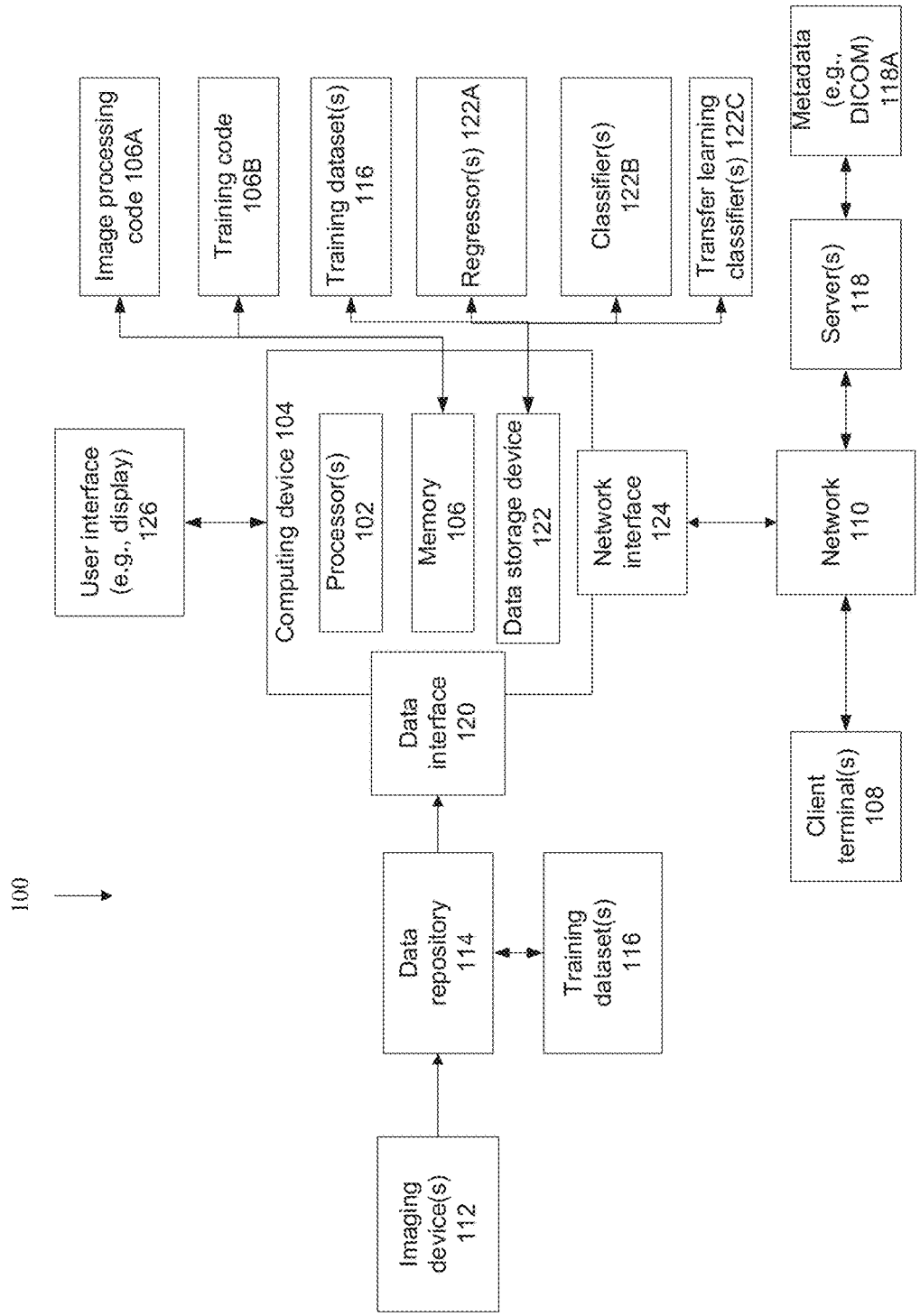
FIG. 1 is a block diagram of a system for training a machine learning model for generating an outcome of a target time interval indicating estimated amount of time from start of contrast administration for an input of a target medical image and/or for inference of the target medical image by the trained machine learning model, in accordance with some embodiments of the present invention.

The present invention, in some embodiments thereof, relates to machine learning (ML) models and, more specifically, but not exclusively, to ML models for analysis of contrast enhanced medical images.

As used herein, the term target time interval and target time value may sometimes be interchanged. For example, a target time value of 5 seconds may also refer to an interval of about 4.5 to 5.5 seconds.

An aspect of some embodiments of the present invention relates to systems, methods, an apparatus, and/or code instructions (stored on a memory and executable by processors(s)) for training a machine learning (ML) model, optionally a neural network based regressor, for generating an outcome indicative of a target time interval and/or target time value indicating estimated amount of time from the start of contrast administration, in response to an input of a target medical image. Medical images of subjects, depicting different contrast phases of contrast administered to the respective subject are accessed. The medical images depict a common body region. For example, CT abdomen scans at different phases of intravenous (IV) contrast administered to the subject are accessed. Metadata indicating respective contrast phase (from multiple candidate contrast phases) is accessed for a first subset of images. For example, DICOM metadata manually entered by a human operator indicating the respective contrast phase is extracted. It is noted that the DICOM metadata may be unreliable, for example, since it is manually entered by an operator and therefore prone to error. A second subset of the medical images may be unassociated with metadata, for example, when no DICOM metadata is available, such as when the operator did not manually enter the metadata. Each respective contrast phase of the first subset of images obtained from the metadata is mapped, optionally by a mapping dataset, to a respective time interval indicating estimated amount of time from a start of contrast administration to time of capture of the respective medical image. The contrast phase may be mapped to a time value within the time interval, optionally the central value within the interval. For example, a non-enhanced contrast phase is mapped to a value of zero seconds, an arterial contrast phase is mapped to a value of 27.5 seconds (which is the central value in the range 20-35 seconds), and a venous contrast phase is mapped to a value of 75 seconds (which is the central value in the range 60-95 seconds). A training dataset is created by labelling images of the first subset with a label indicating the respective mapped time interval and/or time value. The second subset may be included as non-labelled images. The ML model is trained using the training dataset. The trained ML model generates an outcome of a target time interval and/or target time value indicating estimated amount of time from the start of contrast administration, in response to the input of the target medical image.

Optionally, new contrast phases, which were not used in the training dataset are identified. The new contrast phases may represent a form of zero-shot learning capability of the trained ML model, in identifying new contrast phases without having previously seen and/or been trained on the new contrast phases. The new contrast phases may represent new contrast phases that were not extracted from the DICOM metadata. The new contrast phases may represent an adjustment of an existing contrast phase (e.g., in time) and/or division of an existing contrast phase into multiple subphases. A second set of multiple medical images, which are unassociated with metadata indicating contrast phases, and which may have been excluded from the training set used to train the ML model, are accessed. The images of the second set are fed into the trained ML model to obtain outcomes of time intervals and/or time values. The time intervals and/or time values are clustered into multiple clusters. An attempt is made to map the clusters to known contrast phases. Clusters that are non-mapped to known contrast phases are identified. New contrast phases are designated for the images of the non-mapped clusters.

Optionally, the ML model is a first ML model trained on medical images depicting a first body region, for example, CT abdomen images. A second training dataset may be created from a second set of medical images depicting a second body region, for example, CT chest images. A second ML model is trained on the second training dataset using the trained first ML model as an initial state. The second ML model may be trained for high accuracy, even when the number of images of the second set is small, for example, less than about 50, 100, or 200 images.

An aspect of some embodiments of the present invention relates to systems, methods, an apparatus, and/or code instructions (stored on a memory and executable by processors(s)) for automatically tagging a target medical image with an indication of a target time interval and/or target time value indicating estimated amount of time from the start of contrast administration. Alternatively or additionally, the target medical image is automatically tagged with an indication of a contrast phase obtained by mapping the target time interval and/or target time value to the contrast phase. The indication of a target time interval and/or target time value is obtained as an outcome of the trained ML model fed the target medical image.

At least some implementations of the systems, methods, apparatus, and/or code instructions described herein address the technical problem of automated training of ML models for classification of medical images into contrast states. At least some implementations of the systems, methods, apparatus, and/or code instructions described herein address the technical problem of increasing the classification accuracy of ML models that classify medical images into contrast states. At least some implementations of the systems, methods, apparatus, and/or code instructions described herein improve the technical field of ML models, by providing ML models that are automatically trained to classify medical images into contrast states, and/or by increasing accuracy of classification of the ML models. Classification may include a category label indicating the contrast phase, and/or a time value and/or time interval from start of administration of the contrast. The time value and/or time interval may be mapped to a contrast phase category.

At least some implementations of the systems, methods, apparatus, and/or code instructions described herein address the technical problem of automatic generation of labels indicating a contrast phase for medical images (e.g., CT, x-ray images), optionally intravenous (IV) contrast phases. At least some implementations of the systems, methods, apparatus, and/or code instructions described herein improve the field of machine learning, by providing an ML model for automatic generation of labels indicating a contrast phase for medical images, optionally the label indicating a time (e.g., in seconds) from initial administration of contrast.

At least some implementations of the systems, methods, apparatus, and/or code instructions described herein improve upon the existing approach of using manually entered contrast phases stored as metadata in association with medical images (CT scans) used for training an ML model and/or upon standard approaches of manually labelling images used for training an ML model. As described herein, ML models provide a fully automatic contrast phase identification, as categories and/or as time from initial contrast administration. The ML model may be trained without any use of human annotations, using weak labels extracted from (e.g., DICOM) metadata. The ML models described herein automatically generate an outcome of accurately inferred contrast states and/or time from initial contrast administration for medical images (e.g., CT examinations), optionally stored as labels, based upon imaging features of the medical images, independently of associated metadata. In at least some implementations, a zero-shot learning approach is provided to classify contrast enhancement phases which were not previously labeled in the training dataset used to train the ML model, by modeling the delay in seconds following contrast administration. The zero-shot learning approach may increase the accuracy of the ML model identifying contrast phases, but discovering new contrast phases which may be non-standard, such as contrast states that are in-between standard contrast states, and/or sub-states of standard contrast states. The zero-shot approach may be performed by feeding images into the ML model to obtain time values and/or time intervals for the medical images from start of initial contrast administration. The time values and/or time intervals may be clustered. Clusters are mapped back to existing contrast phases. Clusters that are non-mapped to existing contrast phases represent new contrast phases. The new contrast phases may be identified and used to update the ML model to identify the new contrast phases in newly fed medical images. The reliance on information contained in the DICOM headers, restricts the classifier ML model to the phases represented in the DICOM metadata. However, the proposed Zero-Shot learning approach to phase identification based on the regressor ML model, improves upon the classifier ML model, by utilizes the existing phases to generalize to clinical phases not represented in the training dataset, which may also serve as a possible mitigation.

In at least some implementations, transfer learning is used to train a contrast enhancement ML model from a previously trained contrast enhancement ML model on another body region. The second trained ML model by be trained using a small dataset, which by itself may be insufficient for training an ML model. For example, including less than about 50, 100, or 250 images. For example, an ML model for chest CT is trained using an abdominal CT ML model, using little or no labelled chest CT data.

IV contrast administration permits characterization of the quantitative and temporal dynamics of blood flow within an imaged region of interest. These IV contrast enhancement patterns are often critical data in the diagnostic process. Multiphase CT scans acquire images in distinct physiologic vascular time points such as arterial, venous and delayed renal excretory phases. Established multi-phase scan times following IV contrast administration are associated with each such physiologic phases, for example, as described with reference to Adebayo J, Gilmer J, Muelly M, Goodfellow I, Hardt M, Kim B. *Sanity Checks for Saliency Maps*. October 2018. http://arxiv(dot)org/abs/1810(dot)03292 (hereinafter "Adebayo"), incorporated herein by reference in its entirety.

While automatic diagnosis of findings in CT has been subject to much research, for example, as described with reference to Choi K J, Jang J K, Lee S S, et al. *Development and Validation of a Deep Learning System for Staging Liver Fibrosis by Using Contrast Agent-enhanced CT Images in the Liver. Radiology.* 2018; 289(3):688-697. doi:10.1148/radiol.2018180763, and/or Sun C, Guo S, Zhang H, et al. *Automatic segmentation of liver tumors from multiphase contrast-enhanced CT images based on FCNs. Artif Intell Med.* 2017; 83: 58-66. doi: 10.1016/j.artmed.2017.03.008, incorporated herein by reference in its entirety, automatic characterization of the study and series protocol has eluded attention, perhaps because these are data which are generally provided as meta-data and not diagnostic per-se. Information about the particular contrast phase of a CT series relies upon manual entry by a technician and is often partially or inconsistently captured in the DICOM meta-data (e.g., as described with reference to Adebayo). This lack of reliable meta-data has important implications for artificial intelligence (AI) applications in radiology. The absence of accurate and uniform study descriptions may obscure appropriate studies from an algorithmic input filter, resulting in studies which are inappropriately excluded from analysis and/or those which are erroneously analyzed. In either case performance suffers as a result of low yield or unpredictable accuracy. Furthermore, the application of such algorithmic insight will be essential in permitting next-generation fully automatic ML analysis of dynamic radiographic findings capable of discerning, for example, between benign liver fibronodular hyperplasia and malignant hepatocellular carcinoma.

Previous contrast enhancement identification methods have all relied on human based annotations for training, for example, as described with reference to Philbrick K A, Yoshida K, Inoue D, et al. *What Does Deep Learning See? Insights From a Classifier Trained to Predict Contrast Enhancement Phase From CT Images. Am J Roentgenol.* 2018; 211(6):1184-1193. doi:10.2214/AJR.18.20331 (hereinafter "Philbrick"), Dercle L, Lu L, Lichtenstein P, et al. *Impact of Variability in Portal Venous Phase Acquisition Timing in Tumor Density Measurement and Treatment Response Assessment. Metastatic Colorectal Cancer as a Paradigm. JCO Clin Cancer Informatics.* 2017. doi: 10.1200/cci.17.00108 (hereinafter "Derele"), and/or Ma J, Dercle L, Lichtenstein P, et al. Automated Identification of Optimal Portal Venous Phase Timing with Convolutional Neural Networks. *Acad Radiol.* May 2019. doi:10.1016/j.acra.2019.02.024 (hereinafter "Ma"), incorporated herein by reference in its entirety. Dercle proposed systems to quality assess whether a scan was accurately taken in Portal Venous Phase (PVP). The method proposed is semi-automatic and an annotator is expected to manually delineate regions of interest in the scan before it can be analyzed. Ma is limited to indications in the Aorta and the Portal Vein regions. This constraint, however, might drop the overall algorithm performance as described in Dercle. Philbrick is mainly used to examine neural networks visualization approaches in the context of clinical decision making.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
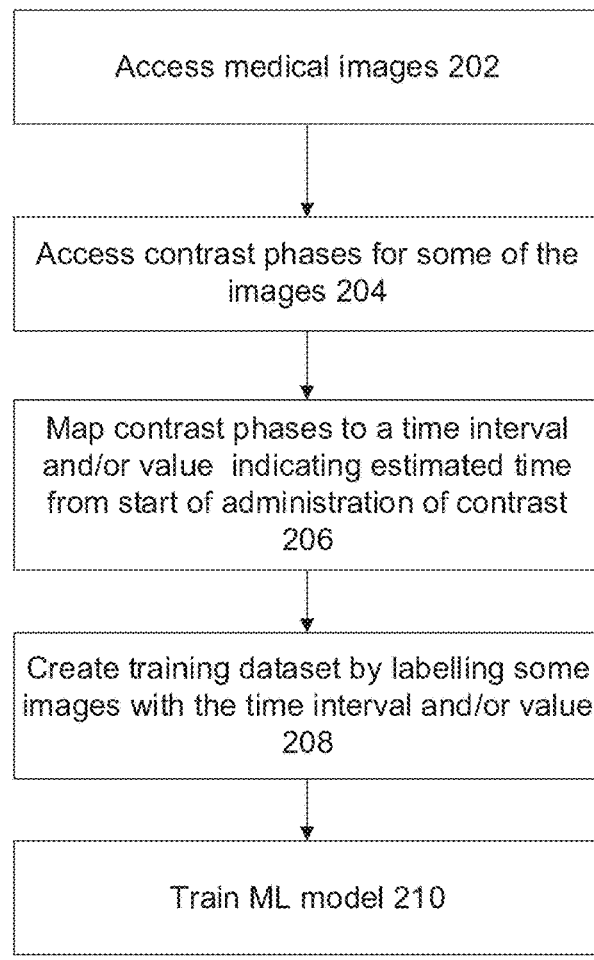
FIG. 2 is a flowchart of a method of training a machine learning model for generating an outcome of a target time interval indicating estimated amount of time from start of contrast administration for an input of a target medical image, in accordance with some embodiments of the present invention.
Figure 3:
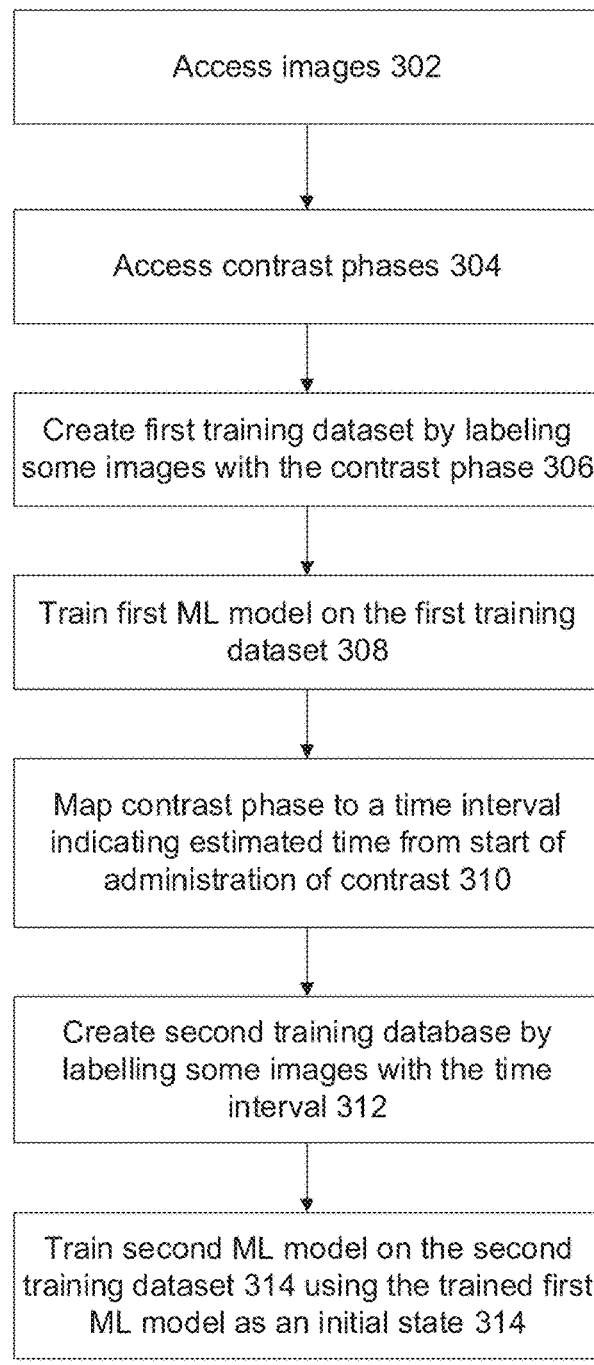
FIG. 3 is a flowchart of another exemplary method of training a machine learning model for generating an outcome of a target time interval indicating estimated amount of time from start of contrast administration for an input of a target medical image, in accordance with some embodiments of the present invention.
Figure 4:
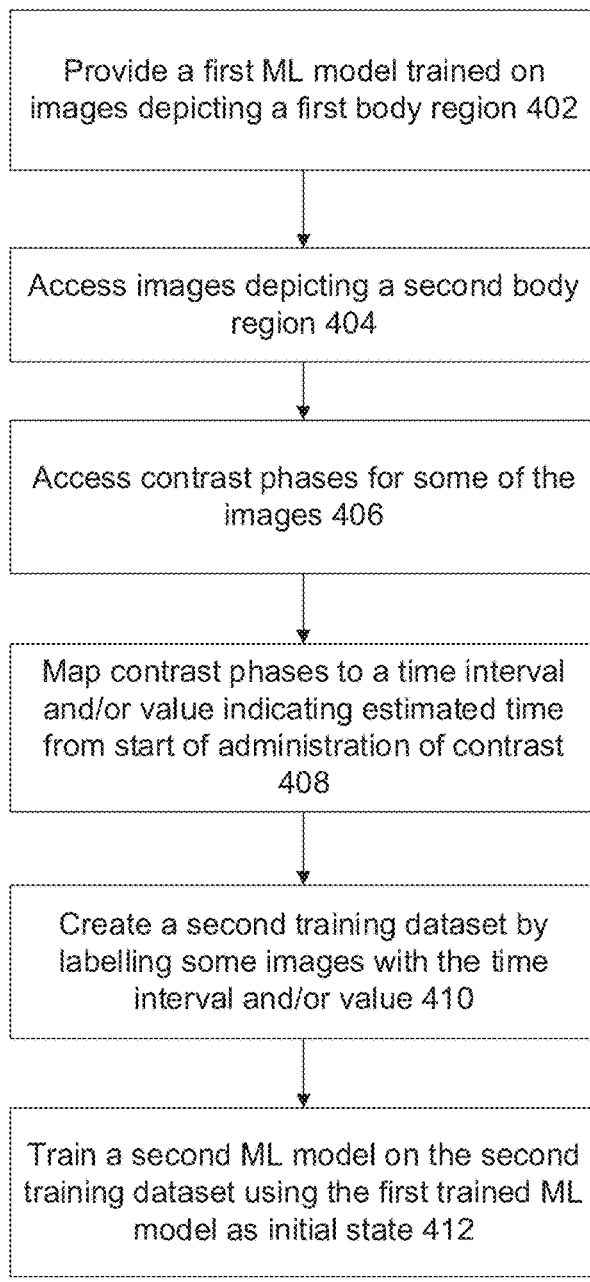
FIG. 4 is a flowchart of a method of training another machine learning model for generating an outcome of a target time interval indicating estimated amount of time from start of contrast administration for an input of a target medical image of a certain body region using a previously trained machine learning model for another body region, in accordance with some embodiments of the present invention.
Figure 5:
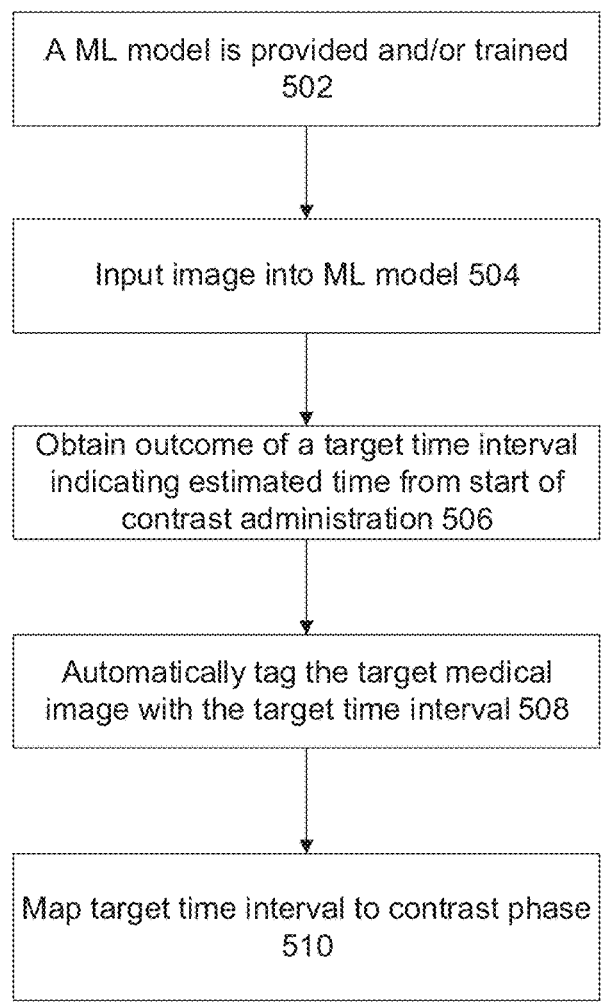
FIG. 5 is a flowchart of a method of generating an outcome of a target time interval indicating estimated amount of time from start of contrast administration for an input of a target medical image by a trained machine learning model, in accordance with some embodiments of the present invention.
Figure 6:
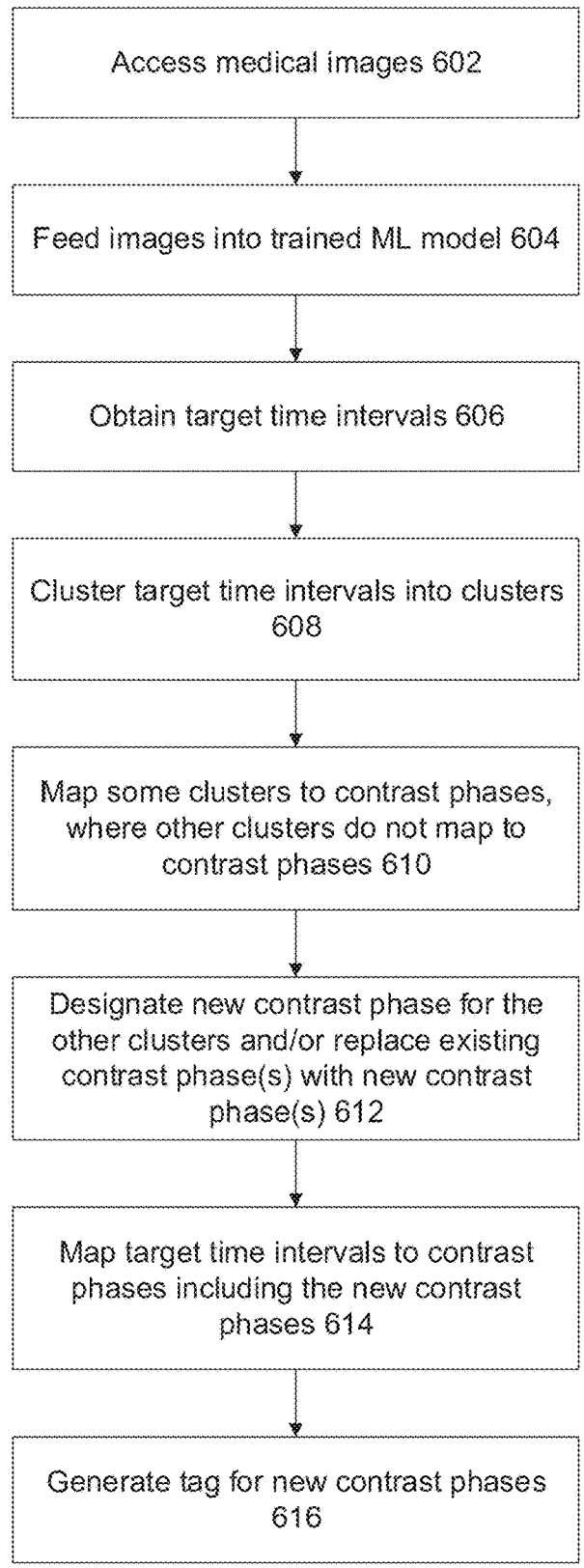
FIG. 6 is a flowchart of a method of zero shot learning of new contrast phase by a trained machine learning model, in accordance with some embodiments of the present invention.

Reference is now made to FIG. 1, which is a block diagram of a system 100 for training a machine learning model for generating an outcome of a target time interval indicating estimated amount of time from start of contrast administration for an input of a target medical image and/or for inference of the target medical image by the trained machine learning model, in accordance with some embodiments of the present invention. Reference is also made to FIG. 2, which is a flowchart of a method of training a machine learning model for generating an outcome of a target time interval indicating estimated amount of time from start of contrast administration for an input of a target medical image, in accordance with some embodiments of the present invention. Reference is also made to FIG. 3, which is a flowchart of another exemplary method of training a machine learning model for generating an outcome of a target time interval indicating estimated amount of time from start of contrast administration for an input of a target medical image, in accordance with some embodiments of the present invention. Reference is also made to FIG. 4, which is a flowchart of a method of training another machine learning model for generating an outcome of a target time interval indicating estimated amount of time from start of contrast administration for an input of a target medical image of a certain body region using a previously trained machine learning model for another body region, in accordance with some embodiments of the present invention. Reference is also made to FIG. 5, which is a flowchart of a method of generating an outcome of a target time interval indicating estimated amount of time from start of contrast administration for an input of a target medical image by a trained machine learning model, in accordance with some embodiments of the present invention. Reference is also made to FIG. 6, which is a flowchart of a method of zero shot learning of new contrast phase by a trained machine learning model, in accordance with some embodiments of the present invention.

System 100 may implement the acts of the method described with reference to FIGS. 2-6, optionally by a hardware processor(s) 102 of a computing device 104 executing code instructions stored in a memory 106.

Computing device 104 may be implemented as, for example, a client terminal, a server, a virtual server, a radiology workstation, a virtual machine, a computing cloud, a mobile device, a desktop computer, a thin client, a Smartphone, a Tablet computer, a laptop computer, a wearable computer, glasses computer, and a watch computer. Computing 104 may include an advanced visualization workstation that sometimes is add-on to a radiology workstation and/or other devices for presenting indications of the identified visual findings and/or other computer added detections to the radiologist.

Computing device 104 may include locally stored software that performs one or more of the acts described with reference to FIGS. 2-6, and/or may act as one or more servers (e.g., network server, web server, a computing cloud, virtual server) that provides services (e.g., one or more of the acts described with reference to FIGS. 2-6) to one or more client terminals 108 (e.g., remotely located radiology workstations, remote picture archiving and communication system (PACS) server, remote electronic medical record (EMR) server) over a network 110, for example, providing software as a service (SaaS) to the client terminal(s) 108, providing an application for local download to the client terminal(s) 108, as an add-on to a web browser and/or a medical imaging viewer application, and/or providing functions using a remote access session to the client terminals 108, such as through a web browser.

Different architectures based on system 100 may be implemented. In one example, computing device 104 provides centralized services. Training of the ML models 122A is performed centrally by computing device 104, as described herein. Inference may be centrally performed by computing device 104. Alternatively, training is performed by another computing device, and inference is centrally performed by computing device 104. Images may be provided to computing device 104 for centralized inference by the trained ML model(s) 122A. Images may be provided to computing device 104, for example, via an API, a local application, and/or transmitted using a suitable transmission protocol. The outcome of the inference may be provided, for example, to client terminal(s) 108 for presentation on a display and/or local storage, used to create a new label for the images which may be stored in an electronic medical record (e.g., DICOM metadata 118A hosted by server 118), stored by computing device 104 and/or used as input into another process (e.g., used to select which images to feed into another classifier, for example, which analyzes the images to detect cancer). In another example, computing device 104 provides centralized training of the ML model(s) 122A, using different training datasets provided by different client terminals 108 and/or servers 118. For example, training datasets originating from different hospitals, and/or training dataset for different imaging modalities, and/or for different body regions. Respective generated ML model(s) may be provided to the corresponding remote devices (e.g., client terminal(s) 108 and/or server(s) 118) for local use. For example, each hospital uses the ML model(s) created from their own training dataset for evaluation of new images captured at the respective hospital, and/or different ML model(s) are locally used to evaluate different medical images generated by different imaging modalities, such as fluoroscopy, voiding studies, and CT scans.

Imaging device 112 provides images, which may be included in training dataset(s) 116 optionally with labels obtained from metadata 118A (e.g., DICOM metadata) (e.g., stored on a PACS implementation of server 118), and/or provided for inference. Image device 112 captures one or more contrast enhanced images at different contrast stages, for example, a 2D, 3D, and/or 4D imaging device, for example, fluoroscopic images depicting contrast injected into blood vessels, a barium study, a voiding study, a swallow study, and CT contrast images depicting various phases of injected intravenous (IV) contrast. 3D images, and/or slices of 3D images, and/or 4D images may be converted to 2D images for training and/or inference, for example, by selecting 2D slices from a 3D scan, and/or converting the 3D image into a 2D image such as by maximum pixel intensity (MPI) approaches. Alternatively, volumes may be used for training and/or inference, for example, multiple sequential CT slices.

Training dataset(s) 116 of images at different contrast phases labelled with labels extracted from metadata (e.g., DICOM metadata) 118A may be stored in a data repository 114, for example, a storage server, a computing cloud, virtual memory, and a hard disk. Training dataset(s) 116 are used to train the ML model(s) 122A, as described herein. It is noted that training dataset(s) 116 may be stored by a server 118, accessibly by computing device 104 over network 110.

Computing device 104 may receive the training dataset(s) 116 (e.g., from data repository 114) and/or obtain images (e.g., from imaging device 112 and/or data repository 114) and/or obtain labels from DICOM metadata 118A of the images, using one or more data interfaces 120, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Hardware processor(s) 102 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 102 may include one or more processors (homogenous or heterogeneous), which may be arranged for parallel processing, as clusters and/or as one or more multi core processing units.

Memory 106 (also referred to herein as a program store, and/or data storage device) stores code instruction for execution by hardware processor(s) 102, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, memory 106 may store image processing code 106A and/or training code 106B that implement one or more acts and/or features of the method described with reference to FIGS. 2-6.

Computing device 104 may include a data storage device 122 for storing data, for example, ML model(s) 122A and/or training dataset(s) 116. Data storage device 122 may be implemented as, for example, a memory, a local hard-drive, a removable storage device, an optical disk, a storage device, and/or as a remote server and/or computing cloud (e.g., accessed over network 110). It is noted that ML model(s) 122A and/or training dataset(s) 116 may be stored in data storage device 122, with executing portions loaded into memory 106 for execution by processor(s) 102.

Computing device 104 may include a network interface 124 for connecting to network 110, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 104 may access one or more remote servers 118 using network 110, for example, to obtain images and/or DICOM metadata 118A to create the training dataset 116, to obtain and/or provide training dataset(s) 116, an updated version of image processing code 106A, training code 106B, and/or the trained ML model(s) 122A.

It is noted that data interface 120 and network interface 124 may exist as two independent interfaces (e.g., two network ports), as two virtual interfaces on a common physical interface (e.g., virtual networks on a common network port), and/or integrated into a single interface (e.g., network interface). Computing device 104 may communicate using network 110 (or another communication channel, such as through a direct link (e.g., cable, wireless) and/or indirect link (e.g., via an intermediary computing device such as a server, and/or via a storage device) with one or more of:

Client terminal(s) 108, for example, when computing device 104 acts as a server providing image analysis services (e.g., SaaS) to remote radiology terminals, for analyzing remotely obtained anatomical images using the trained ML model(s) 122A.

Server 118, for example, implemented in association with a PACS, which may store training dataset(s) 116 and/or may store captured images for inference and/or store metadata 118A (e.g., DICOM metadata) used to extract labels indicating contrast phase of respective images.

Imaging device 112 and/or data repository 114 that store images acquired by imaging device 112. The acquired images may be fed into trained ML model(s) 122A for inference thereof, and/or labelled with metadata 118A indicating contrast phase for generating training dataset(s) 116.

Computing device 104 and/or client terminal(s) 108 and/or server(s) 118 include and/or are in communication with a user interface(s) 126 that includes a mechanism designed for a user to enter data (e.g., patient data) and/or view the outcome of the inference of the captured image(s), for example, seconds from initial contrast administration and/or contrast label. Exemplary user interfaces 126 include, for example, one or more of, a touchscreen, a display, a keyboard, a mouse, and voice activated software using speakers and microphone.

Referring now back to FIG. 2, at 202, medical images of multiple subjects are accessed. The medical images depict a common body region (e.g., chest, pelvis, abdomen) at various contrast phases of contrast administered to the respective subject. For example, the medical images are CT scans depicting various phases of intravenous (IV) contrast administered to the respective subject.

The contrast may be vascular (e.g., IV), and/or non-vascular (e.g., gastro-intestinal, urine).

Other examples of images and contrast include: barium swallow gastro intestinal x-ray studies, x-ray voiding studies, x-ray angiography (at different body vessels, such as brain, peripheral vessels, femoral artery, and the like.

Medical images may be, for example, 3D images, 2D slices of a 3D volume, and/or sequentially captured 2D images (e.g., video, and/or sequence of still images, such as fluoroscopic images and/or barium study and/or voiding study).

Optionally, when the medical images are three (3D) dataset, an input representation of the 3D dataset is extracted. The input representation may be a 2D image. The input representation is included in the training dataset used to train the machine learning model, and/or the input representation is used during inference. Exemplary input representations include: a single two dimensional (2D) slice selected from a plurality of slices of the 3D dataset, a maximum intensity projection (MIP) in a selected plane computed from the 3D dataset, and a volumetric subset selected from the 3D dataset.

At 204, an indication of a respective contrast phase is accessed for each images of a first subset of the medical images. The respective contrast phase is one of multiple candidate contrast phases, which may be defined based on standard clinical practice guidelines. The indication of the respective contrast phase may be obtained (e.g., automatically) from metadata associated with the medical image, for example, DICOM free text stored as metadata. The indication may be manually entered by a technician performing the CT scan. The indication may be automatically extracted from a radiology report of the radiologist that read the CT scan. The indication may be automatically entered as metadata, for example, obtained from an automatic IV contrast injection device.

A second subset of the medical images are each unassociated with the indication of the respective contrast phase, for example, the respective contrast phase is unavailable, such as when there is no DICOM free text.

At 206, respective contrast phases associated with the first subset of medical images are mapped to respective time intervals (e.g., ranges) and/or to specific respective time values (e.g., time in seconds). Each time interval and/or time value indicates an estimated amount of time from a start of contrast administration to time of capture of the respective medical image. It is noted that other start reference baselines may be used. The specific time value may be, for example, a midpoint within an estimated respective time interval. The respective time interval may be based on empirical clinical evidence, such as when the contrast phase is expected to appear in a population of subjects. The mapping may be performed, for example, according to a predefined mapping function, and/or a mapping dataset. For example: a non-enhanced contrast phase is mapped to a value of zero seconds, an arterial contrast phase is mapped to a value of 27.5 seconds within an approximate time interval of 20-35 seconds, a venous contrast phase is mapped to a value of 75 seconds within an approximate time interval of 60-90 seconds, and a delayed contrast phase is mapped to a value of 480 seconds within an approximate time interval of 6-10 minutes.

At 208, a training dataset is created by labelling the images of the first subset of images with a label indicating the respective time interval and/or specific respective time value. The training dataset may further include the second subset of images as non-labelled images. The training dataset may include a portion of labelled images and another portion of unlabeled images.

At 210, a machine learning model is trained using the training dataset. The trained machine learning model receives an input of a target medical image of a subject depicting the common body region at an unknown contrast state, and generates an outcome of a target time interval and/or specific time value indicating estimated amount of time from the start of contrast administration.

Optionally, the machine learning model is implemented as a regressor.

An exemplary architecture of the machine learning model is now described. The machine learning model may be implemented as a convolutional neural network (CNN). The CNN may include 12 convolutional layers. Each layer may include a filter of size 3×3 and stride 1. After every 2 convolutions, downsampling by max-pooling is performed with kernel size 2×2 and stride 2. The first 2 convolutional layers have 16 filters. The number of filters is doubled after each downsampling layer except for the last 2 convolutional layers, which each include 256 filters. A global max-pooling layer is applied to the final feature maps and output to a single output node. Batch normalization (BN) is applied after each convolution before rectified linear unit activation (ReLU).

Referring now back to FIG. 3, at 302, images are accessed, for example, as described with reference to 202 of FIG. 2.

At 304, indications of respective contrast phases are accessed for a first subset of the images. For a second subset, no indications of respective contrast phases may be obtained, for example, no DICOM metadata indicating the contrast phases is available. For example, as described with reference to 204 of FIG. 4.

At 306, a first training dataset is created by labelling images of the first subset of images with respective label indicating the respective contrast phase. The labels may be, for example, classification labels (e.g., text, code) indicating a specific contrast phase from multiple candidate predefined contrast phases. The labels may include errors and/or inaccuracies, representing weak labels for the first training dataset. For example, when the labels are manually entered by a user, the user may make a mistake in the respective contrast phase (e.g., entering an incorrect contrast phase), and/or the user may omit the contrast phase entirely (i.e., no contrast phase is provided). The second subset of images may be included in the first training dataset as non-labelled images.

At 308, a first ML model is trained using the first training dataset. The first ML model generates an outcome of a certain classification label indicating a certain contrast phase selected from the multiple candidate classification labels indicating multiple contrast phases, in response to an input of a target medical image.

The first ML model may be trained using a semi-supervised classification training approach, optionally when the first training dataset includes the weak labels and/or includes the second subset of non-labelled images.

At 310, respective contrast phases associated with the first subset of medical images are mapped to respective time intervals (e.g., ranges) and/or to specific respective time values (e.g., time in seconds), For example, as described with reference to 208 of FIG. 4.

At 314, a second ML model is trained on the second training dataset by using the first ML model as an initial state.

Optionally, the first ML model is implemented as a classifier, and the second ML model is implemented as a regressor. The first ML model may be adapted to a regressor, and using the initial weights of the trained first ML model, the adapted first ML model is further trained on the second training dataset to obtain the trained second ML model.

Optionally, the first ML model and the second ML model are implemented using a common convolutional neural network (CNN) architecture. The first ML model may include an output layer with multiple outputs corresponding to the multiple contrast phases (e.g., the multiple classification labels indicating the multiple contrast phases). The second ML model may include an output layer with a single output corresponding to the target time interval and/or the time value. Weights of the second ML model prior to training are initialized with weights of the trained first ML model. The second ML model may be created by adapting the output layer of the trained single ML model, from multiple outputs to the single output, and further training on the second training dataset.

Referring now back to FIG. 4, at 402, a first ML model trained on medical images depicting a first body region is provided. The first body region may be, for example, chest, abdomen, pelvis.

The first ML model may be trained, for example, as described with reference to FIGS. 2 and/or 3.

At 404, images depicting a second body region are accessed, for example, as described with reference to 202 of FIG. 2. For example, the first ML model is trained on CT abdomen medical images, and the second training dataset, for training the second ML model, includes CT chest medical images. In another example, the first ML model is trained on CT chest medical images, and the second training dataset, for training the second ML model, includes CT abdomen medical images.

At 406, indications of respective contrast phases are accessed for a first subset of the images depicting the second body region. For a second subset, no indications of respective contrast phases may be obtained, for example, no DICOM metadata indicating the contrast phases is available. For example, as described with reference to 204 of FIG. 2.

At 408, respective contrast phases associated with the first subset of medical images depicting the second body region are mapped to respective time intervals (e.g., ranges) and/or to specific respective time values (e.g., time in seconds), for example, as described with reference to 206 of FIG. 2.

At 410, a second training dataset is created by labelling the images of the first subset of images depicting the second body region with a label indicating the respective time interval and/or specific respective time value. The training dataset may further include the second subset of images depicting the second body region as non-labelled images. The training dataset may include a portion of labelled images and another portion of unlabeled images. For example, as described with reference to 208 of FIG. 2.

Optionally, the second training dataset includes significantly fewer images than the first training dataset used to train the first ML model. For example, the second training dataset includes less than about 25, 50, 100, 150, or 250 (or other values) medical images, and the first training dataset includes over about 1000, or 10000, or 25000 (or other values) medical images.

At 412, a second ML model is trained on the second training dataset, using the trained first ML model as an initial state. For example, the second ML model is the first ML model that is further trained on the second training dataset. In another example, the second ML model is an adapted architecture of the first ML model, where weights of the trained first ML are used to initialize the adapted architecture, which is then further trained on the second training dataset.

The first and/or second ML models may be implemented as regressors, optionally CNN, for example, using the exemplary architecture described herein.

The first ML model and the second ML model may share a common feature space with similarities in distribution of features associated with contrast enhancement in images depicting the first body region and images depicting the second body region. For example, when the first ML model is trained on CT chest images, and the second ML model is trained on CT abdomen chest images, both chest and abdomen images depict different regions of the aorta which have similar contrast phase profiles.

Referring now back to FIG. 5, at 502, a ML model is provided and/or trained, for example, as described with reference to FIG. 2-4.

At 504, a target medical image is accessed, and fed into the ML model.

Optionally, when the medical image is a three (3D) dataset, a 2D input representation of the 3D dataset is extracted and fed into the ML model. Exemplary input representations are described, for example, with reference to 202 of FIG. 2.

At 506, an outcome of a target time interval and/or time value indicating estimated amount of time from start of contrast administration is obtained from the ML model.

At 508, the target medical image may be automatically tagged with a tag indicating the target time interval and/or time value. For example, the tag may be automatically documented as metadata associated with the target medical image, for example, DICOM metadata.

At 510, the target time interval and/or time value is mapped to a specific contrast phase. Mapping may be performed, for example, using the mapping described with reference to 206 of FIG. 2, in the opposite direction.

The target medical image may be automatically tagged with a tag indicating the specific contrast phase. The indicating the specific contrast phase may be in addition to, or alternatively to the tag indicating the target time interval and/or time value. For example, the tag indicating the specific contrast phase may be automatically documented as metadata associated with the target medical image, for example, DICOM metadata.

Optionally, when metadata such as DICOM metadata documenting a contrast phase for the target medical image already exists (e.g., manually entered by a user, such as the technician that performed the CT scan), the computed tag indicating the target time interval and/or time value may overwrite the existing metadata and/or be added as additional metadata. Optionally, when metadata such as DICOM metadata documenting a contrast phase for the target medical image already exists (e.g., manually entered by a user, such as the technician that performed the CT scan), the computed tag indicating the specific contrast phase may be used to overwrite the existing DICOM metadata, such as when the contrast phase of the tag is different than the existing contrast phase of the metadata. This is based on the observation of the high error rate of existing DICOM metadata, such as due to errors during manual entry.

Referring now back to FIG. 6, at 602, a second set of medical images of a second set of subjects is accessed. The second set of medical images depict subjects are different contrast phases and are unassociated with respective contrast phases, for example, no metadata (e.g., DICOM metadata) indicating contrast phases is available. The contrast state of the second set of medical images is unknown.

Alternatively, the contrast phases are available (e.g., as metadata, such as DICOM metadata) for at least some of the images. The available contrast phases may be ignored in further processing, for example, based on the assumption that the existing contrast phases are incorrect, such as due to manual errors during input and/or Inventor's observation of the high rate of error in existing DICOM metadata contrast phases.

The second set may be different than the images used to train the ML model.

At 604, the second set of medical images (e.g., each image) is fed into the ML model.

At 606, target time intervals and/or target values are obtained as outcomes of the ML model for each inputted medical image.

At 608, the target time intervals and/or target values are clustered into multiple clusters.

Clustering may be performed, for example, using non-supervised approaches, grouping target time interval and/or target values into common intervals and/or values, and/or plotting a histogram of the time intervals and/or values, and clustering based on peaks and distributions of the histogram.

At 610, a first subset of clusters (i.e., images belonging to each cluster) is mapped to predefined contrast phases. Alternatively, the first set of clusters is not explicitly mapped, but determined to be able to be mapped, where the mapping is delayed until 612.

The predefined contrast phases may be, for example, the set of contrast phases defined by the DICOM metadata, and/or the set of contrast phases defined by the mapping used to create the training dataset for training the ML model.

Mapping may be performed, for example, using the mapping described with reference to 206 of FIG. 2, using the contrast phases defined by the mapping, in the opposite direction.

Exemplary Contrast Phases Include: Not Enhanced, Arterial Phase, Venous Phase, and Delayed Phase Optionally, a second subset of the clusters (i.e., images belonging to those clusters) is non-mapped to the contrast phases. For example, the time interval and/or time value of the second subset does not correspond to any of the defined contrast phases. For example, no mapping exists in the mapping dataset.

At 612, one or more new contrast phases are designated for the second subset of clusters, which have not been mapped to any of the previously defined contrast phases. The new contrast phase(s) may be an entirely new category of contrast phase which has not previously been defined, for example, covering a time interval and/or time value which was previously not mapped to a previously defined contrast phase. For example, a nephrogenic phase between the venous phase and delayed phase discovered by Inventors (as described in the Examples section below).

Alternatively or additionally, the new contrast phase(s) replace and/or redefine previously defined contrast phase(s), for example, an existing contrast phase is split into two or more new contrast phases. In another example, the mapping between time intervals and/or time values for one or more existing contrast phases is adjusted, for example, the time interval corresponding to a certain contrast phase is lengthened, shortened, or moved to higher or lower values. For example, new early arterial and late arterial phases replacing the existing arterial phase discovered by Inventors (as described in the Examples section below).

Identification of the new contrast phases may represent a zero-shot learning capability of the trained ML model described herein.

The mapping dataset that maps between time intervals and/or time values, and contrast phases, is updated to include the new contrast phase(s).

Optionally, the first subset of the clusters (i.e., images belonging to those clusters) are re-mapped, or when mapping was delayed, are now mapped, using the updated mapping dataset that includes the new contrast phases(s). The second subset of clusters (i.e., images belonging to those clusters) may be mapped using the updated mapping dataset that includes the new contrast phases(s).

An example of an updated mapping dataset discovered by Inventors (as described in the Examples section below) includes: mapping a target time interval of zero to all phases before injection, mapping the target time interval of 15-20 seconds to early arterial contrast phase, mapping the target time interval of 20-35 seconds to later arterial contrast phase, mapping the target time interval of 60-90 seconds to hepatic portal venous contrast phase, mapping the target time interval of 100-200 seconds to nephrogenic contrast phase, and mapping the target time interval of 6-10 minutes to delayed contrast phase.

At 614, the target time interval and/or target value may be mapped to one of the contrast phases including the new contrast phase(s) by the updated mapping dataset.

At 616, a tag indicating the contrast phase mapped using the updated mapping dataset may be created for each of the images of the first and/or second subset.

Optionally, the updated mapping dataset is provided for updating the ML model and/or classifier described herein, for generating outcomes for new target images that include the new contrast phases.

Various embodiments and aspects of the present invention as delineated herein above and as claimed in the claims section below find experimental and/or calculated support in the following examples.

EXAMPLES

Reference is now made to the following examples, which together with the above descriptions illustrate some embodiments of the present invention in a non-limiting fashion.

Inventors conducted experiments based on at least some implementations described herein, to evaluate the application of ML models to automatically identify the presence and physiologic phase of intravenous (IV) contrast in Computed Tomography (CT) scans of the Chest, Abdomen and Pelvis. Training, testing and validation data were acquired from a dataset of 82,690 chest and abdomen CT examinations performed at 17 different institutions. Free text in DICOM metadata was utilized as weak labels for semi-supervised classification training. Contrast phase identification was approached as a classification task, using a 12-layer CNN and ResNet18 with four contrast-phase output. The ML model was reformulated to fit a regression task aimed to predict actual seconds from time of IV contrast administration to series image acquisition. Transfer learning was used to optimize the ML model to predict contrast presence on CT Chest. By training based on labels inferred from noisy, free text DICOM information, contrast phase was predicted with 93.3% test accuracy (95% CI: 89.3%, 96.6%). Regression analysis resulted in delineation of early vs late arterial phases and a nephrogenic phase in between the portal venous and delayed excretory phase. Transfer learning applied to Chest CT achieved an AUROC of 0.776 (95% CI: 0.721, 0.832) directly using the model trained for abdomen CT and 0.999 (95% CI: 0.998, 1.000) by fine-tuning. The presence and phase of contrast on CT examinations of the Abdomen-pelvis accurately and automatically be ascertained by a machine learning model. Transfer learning applied to CT Chest achieves high precision with as little as 100 labeled samples.

Materials and Methods

Data

A proprietary dataset of 1,754,319 (408,738 patients) chest and abdomen CT scans from 17 different institutions was utilized for training, testing and validation (80%, 10%, and 10%, respectively.) All Patient Health Information (PHI) was removed from the data prior to acquisition, in compliance with HIPAA standards. The axial slices of all scans have an identical size of 512×512, but the number of slices in each scan vary between 42 and 1026, with slice spacing ranging from 0.45 mm to 5.0 mm. No image reformatting or standardization was performed. To obtain ground truth labels for training and validation, the free text information of the DICOM header SeriesDescription which was found to contain information indicative of the contrast phase at the series level was utilized. The completeness of the DICOM header varied widely both within and among institutions. Regular expressions were used to weakly label the phase of each scan as: Non enhanced, Arterial, Portal Venous, Delayed. Scans which were not axial and did not contain the abdomen regions of interest were then filtered. The final set consisted of 61,706 scans (33,696 patients) for training, 13,961 validation (6,043 patients) and 9,165 (4,588 patients) for testing.

Figure 7:
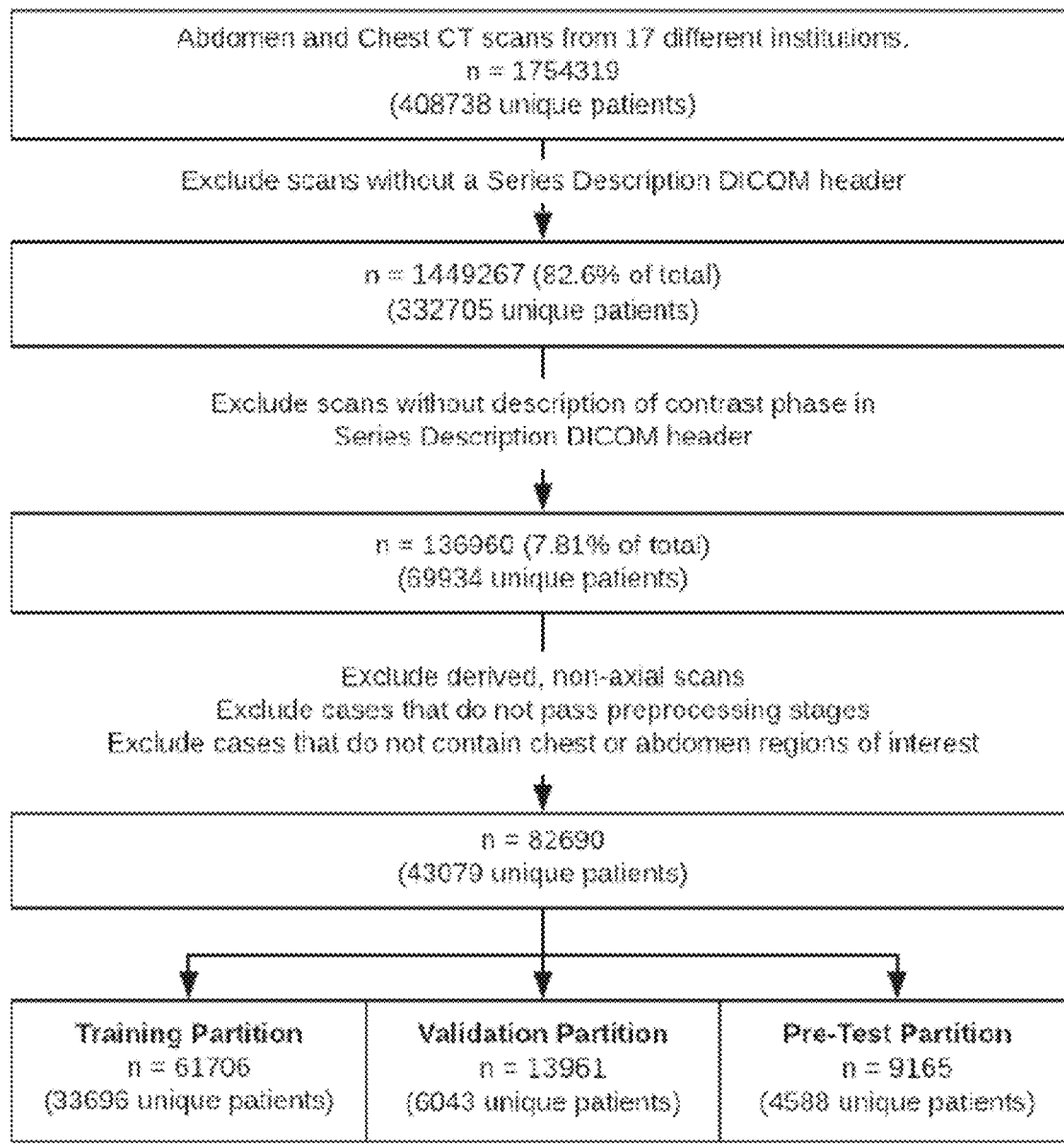
FIG. 7 is a flowchart depicting a process for data acquisition and information regarding the availability of DICOM metadata, as part of the experiment, in accordance with some embodiments of the present invention.

Reference is now made to FIG. 7, which is a flowchart depicting a process for data acquisition and information regarding the availability of DICOM metadata, as part of the experiment, in accordance with some embodiments of the present invention. To curate data for this experiment, CT scans were acquired from 17 different institutions, scans which were found to be non-compliant for this experiment were excluded, and the data was partitioned into three folds: train, validation and test. For evaluation of model performance, CT scans were sampled from the held-out test set and manually labeled by an expert radiologist.

Figure 8:
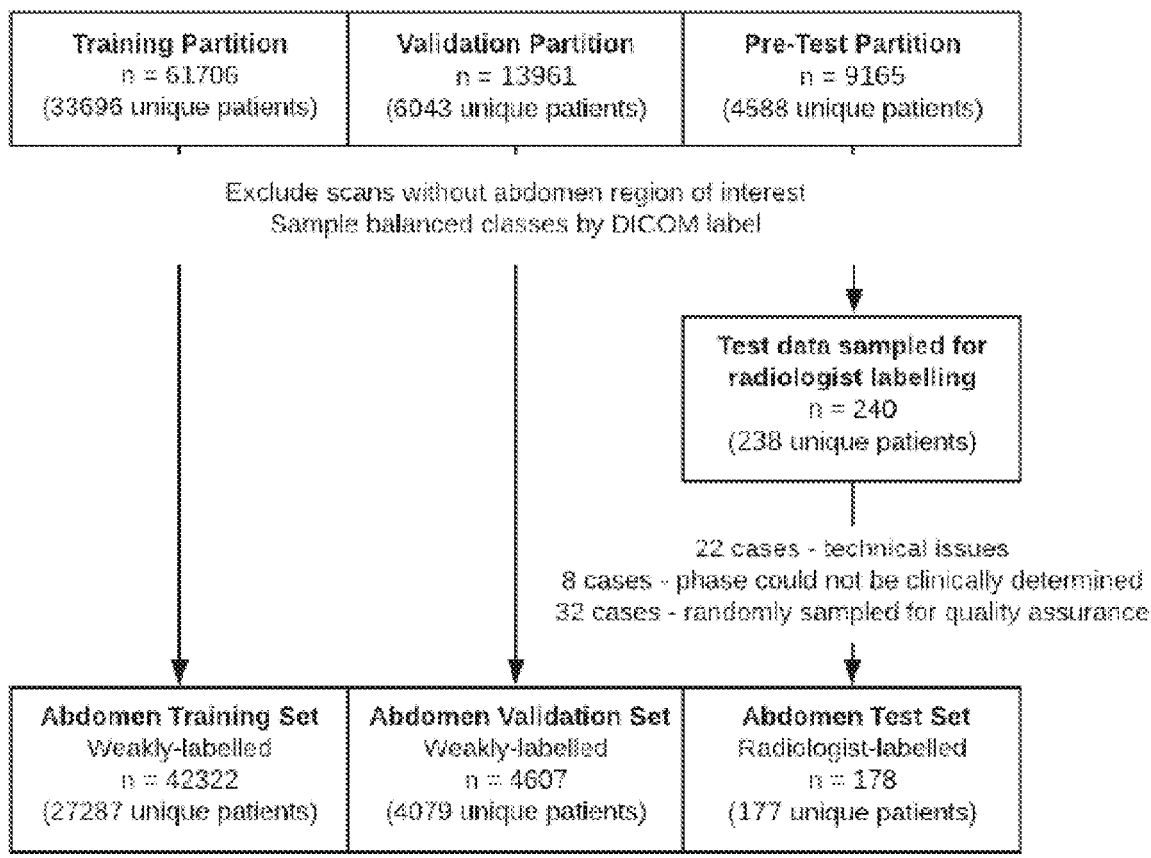
FIG. 8 is a flowchart depicting a process for curating data for abdominal CT scans, using a sampling protocol and exclusion of CT scans, as part of the experiment, in accordance with some embodiments of the present invention.

Reference is now made to FIG. 8, which is a flowchart depicting a process for curating data for abdominal CT scans, using a sampling protocol and exclusion of CT scans, as part of the experiment, in accordance with some embodiments of the present invention. CT Abdomen scans were sampled equally from each phase, according to the labels extracted from the DICOM metadata. Within each phase, the four most prevalent institutions were equally represented. The final test set consisted of 178 scans (177 patients), each labeled by a radiologist as non-enhanced, arterial, portal venous and delayed.

Figure 9:
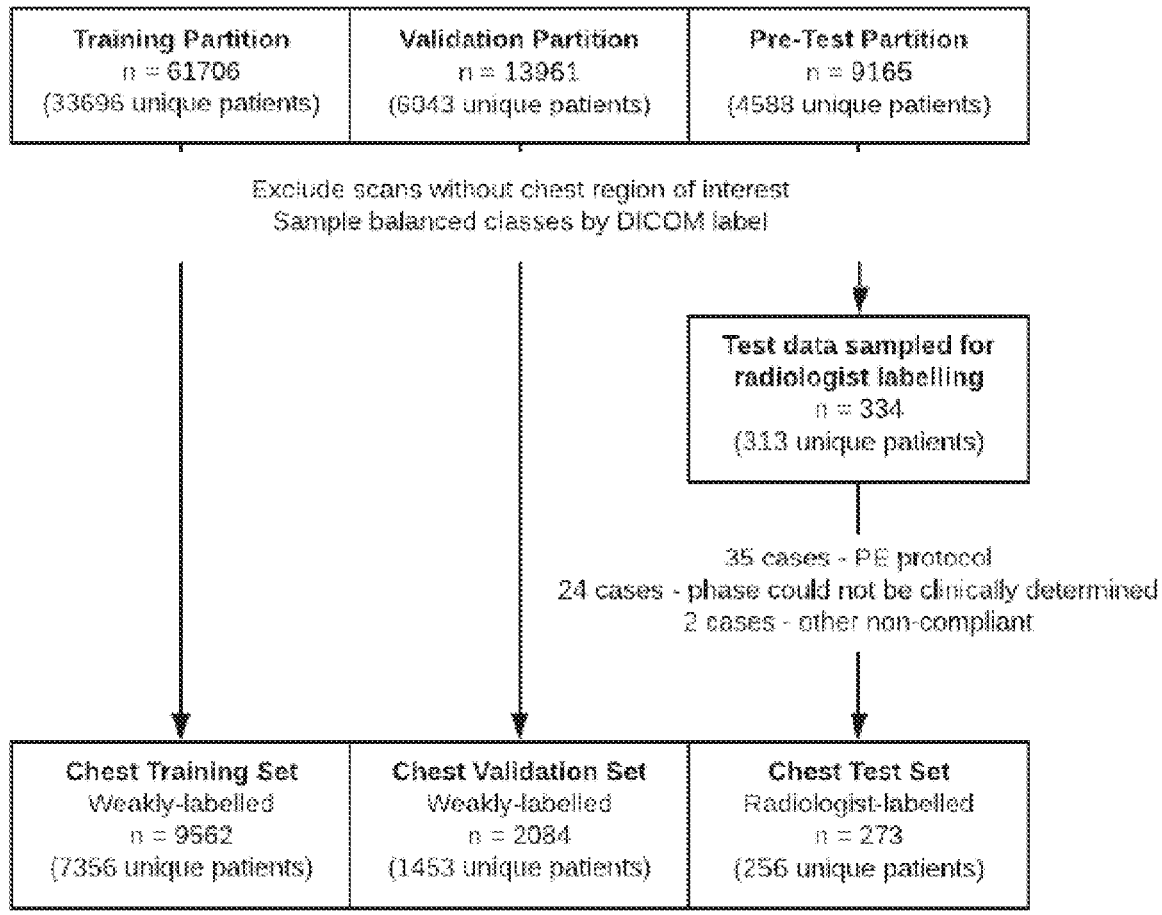
FIG. 9 is a flowchart depicting a process for curating data for chest CT scans, using a sampling protocol and exclusion of CT scans, as part of the experiment, in accordance with some embodiments of the present invention.

Reference is now made to FIG. 9, which is a flowchart depicting a process for curating data for chest CT scans, using a sampling protocol and exclusion of CT scans, as part of the experiment, in accordance with some embodiments of the present invention. Scans were sampled according to the labels extracted from the DICOM metadata from the non-enhanced, pulmonary arterial, and systemic venous phases as well as from unlabeled scans partition. A test set for chest CT consisted of 273 scans (256 patients) each labeled by a radiologist as non-enhanced, pulmonary arterial, and systemic venous phases.

Methods

Contrast phase identification was approached as a classification task, training a convolutional neural network (CNN) classifier (also referred to herein as classifier ML model) with four output classes corresponding to the 4 IV contrast phases described in the DICOM metadata, as described herein.

A region of interest was automatically localized for each CT scan using an algorithmic approach similar to, for example, as described with reference to Sahiner B, Pezeshk A, Hadjiiski L M, et al. *Deep learning in medical imaging and radiation therapy. Med Phys.* 2019; 46(1):e1-e36. doi: 10.1002/mp.13264, incorporated herein by reference in its entirety. This ensures that a similar anatomical region is extracted for each scanned individual, independent of factors specific to any scanning protocol such as the total number of reconstructed CT slices or slice thickness. To optimize visual representation of IV contrast phase information, the volume selected contained the liver, kidneys, aorta, and inferior vena cava (IVC), for example, as described with reference to Guite K, Louis L, Lee F. *Computed Tomography in Abdominal Imaging: How to Gain Maximum Diagnostic Information at the Lowest Radiation Dose. In: Selected Topics on Computed Tomography. InTech;* 2013. doi:10.5772/55903 (hereinafter "Guite"), incorporated herein by reference in its entirety.

Three different approaches of representing the full CT volume for contrast phase classification were compared: single slice, maximum intensity projection (MIP) in the axial plane, and volumetric representation. For the single-slice and MIP input methods, the ML model receives single-channel images of size 512×512×1. For volumetric input representations, 512×512×5 volumes are received by the ML model, with each channel being one of the sampled slices.

The classifier ML model includes 12 convolutional layers, each with filter size 3×3 and stride 1. After every 2 convolutions, downsampling by max-pooling is performed with kernel size 2×2 and stride 2. The first 2 convolutional layers have 16 filters, with the number of filters doubled after each downsampling layer (except for the last 2 convolutional layers, which include 256 filters each). A global max-pooling layer is applied to the final feature maps and output to a 4-way softmax. Batch normalization (BN) is applied after each convolution before rectified linear unit activation (ReLU), for example, as described with reference to Ioffe S, Szegedy C. *Batch Normalization: Accelerating Deep Net-* work *Training by Reducing Internal Covariate Shift*. February 2015. http://arxiv(dot)org/abs/1502.03167, incorporated herein by reference in its entirety.

The ML model described herein was benchmark against ResNet18, for example, as described with reference to He K, Zhang X, Ren S, Sun J. *Deep Residual Learning for Image Recognition*. December 2015, http://arxiv(dot)org/abs/1512 (dot)03385, (hereinafter "He") incorporated herein by reference in its entirety.

Augmentations performed during training include: random scaling by a factor of ±0.2, translation by factor of ±0.0625, vertical and horizontal flips, shearing and rotation of ±20°, and additive Gaussian noise with standard deviation of 0.2. Each augmentation is independently applied with probability 0.5.

Training each model took less than 1 day using a single NVIDIA Titan X GPU with 12 GB memory, using Keras 2.1.3 over Tensorflow 1.3. The Adam optimizer was used with a learning rate of 0.0001 and default Keras parameters, using a batch size of 32 with random sampling. Training was performed for 40 k iterations, measuring loss and accuracy on the validation set every 400 iterations. The ML model from the epoch with the best validation accuracy was saved.

To extend the approach to more fine-grained information about the contrast enhancement phase of each scan, a Zero-Shot learning approach to phase identification, which utilizes the existing phases to generalize to clinical phases not represented in the training dataset, was implemented. To achieve this, the phase identification task was modelled as a regression problem to predict a single value indicating the degree of progression of the contrast agent—in this case, a natural approach is to consider the scan delay in seconds from the time of injection of IV contrast. Assuming all other factors are constant, a noisy scan acquisition time was defined for each phase, based on general timings (e.g., as described with reference to Guite), and associated free text in each series' DICOM descriptions.

Reference is now made to FIG. 10, which is a table of general scan acquisition time delays used for obtaining different contrast phases for training a regression ML model, as part of the experiment, in accordance with some embodiments of the present invention.

The regression ML model was created by modifying the architecture of the ML model classifier described above, replacing the 4-way softmax layer with a single output node. Weights are initialized using the trained classification ML model (not including the output layer). A 12-loss is used to train the regression ML model and similar training parameters are used from the classification approach.

To explore the value of freely available labels in a new, separate task, chest CT contrast enhancement was considered. This problem is closely related to abdomen contrast phase identification, in that both tasks share the same feature space and there are potentially some similarities in the distribution of features associated with contrast enhancement, such as enhancement of the aorta. The phases themselves can be considered a subset of the abdomen phases, and include non-enhanced, pulmonary-arterial, and systemic venous phases (delayed venous phase images are generally acquired to evaluate the urinary system and thus not found in chest CT imaging). For simplicity, a binary classifier between contrast-enhanced and non-enhanced scans was considered for evaluating the benefit of transfer learning.

First, an attempt was made to directly predict the contrast phase in chest scans using an ML model trained only on abdomen CT samples, to explore whether similarities in feature distributions would allow the phase to be directly inferred in the new domain. Performance was compared between chest contrast phase classifiers trained with random weight initialization and with weights initialized from the trained abdomen ML model, incrementing the number of training samples available.

For all statistical analysis, scikit-learn (version 0.20; scikit-learn(dot)org) in Python 3.6.8 was used. To compare AUCs, DeLong test (e.g., as described with reference to Sun X, Xu W. *Fast implementation of DeLong's algorithm for comparing the areas under correlated receiver operating characteristic curves. IEEE Signal Process Lett.* 2014. doi: 10.1109/LSP.2014.2337313, incorporated herein by reference in its entirety) was used (P 0.05 indicated statistical significance) and for all other statistics, to obtain confidence intervals (CIs) bootstrap (n=10,000) was used.

Results

Abdomen Contrast Phases Classification.

Reference is now made to FIG. 11, which is a table presenting Abdomen CT contrast enhancement phase classifier performance results using the 12-layer CNN ML classifier and ResNet 18 architectures, for the experiment, in accordance with some embodiments of the present invention. Presented data are the accuracy and the number of correctly predicted cases for each ML model and input type. In parentheses are 95% confidence intervals. Evaluation of the ML model on the validation dataset is based on weak labels extracted from DICOM metadata while the evaluation on the test dataset are based on labels which were manually assigned by a US board certified Radiologist (EE). The best result was obtained using a volumetric input and a 12-layer CNN, achieving 93.3% (166 of 178; 95% CI: 89.3%, 96.6%) test accuracy.

Figure 12:
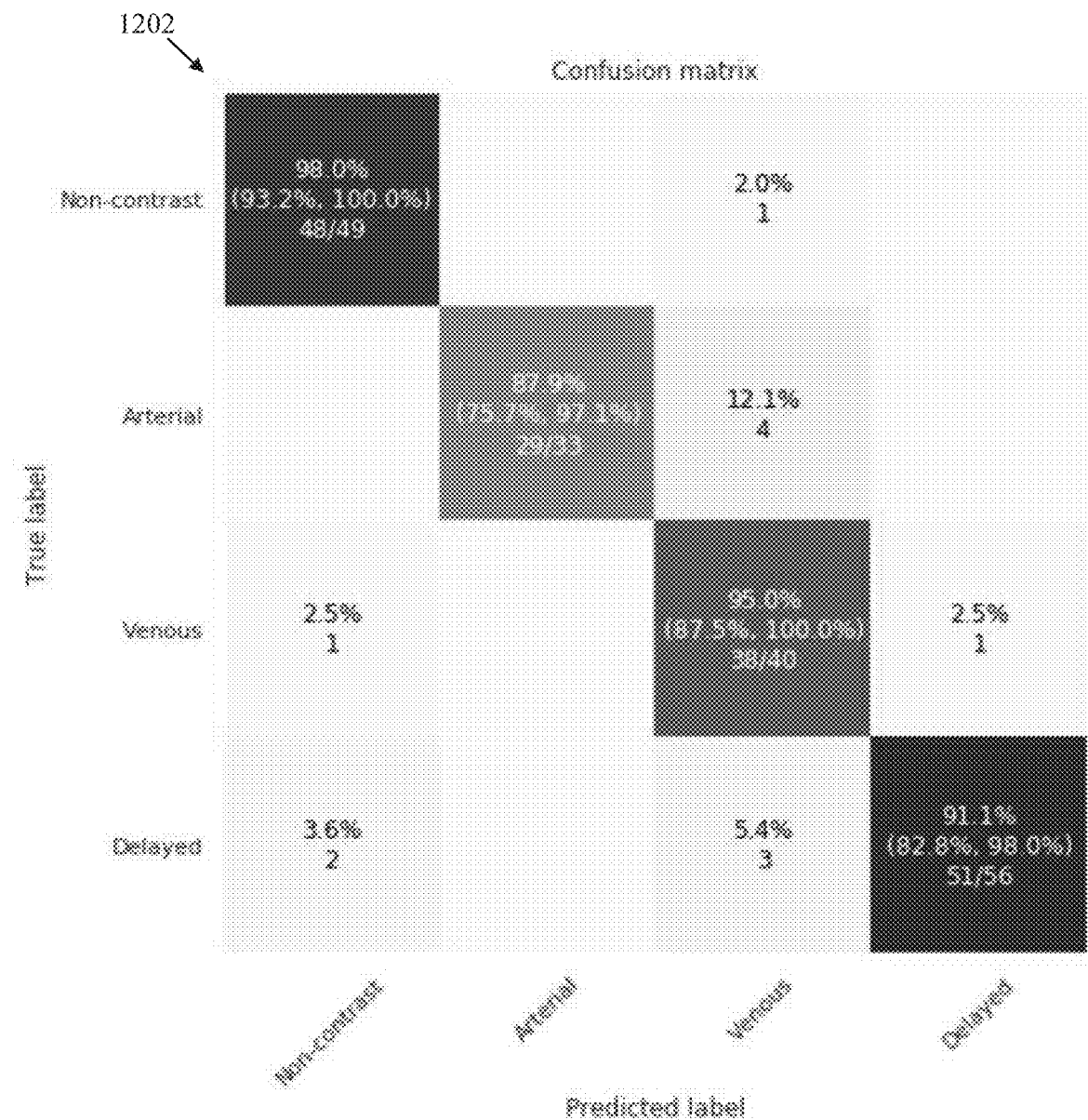
FIG. 12 is a confusion matrix for CT abdomen with contrast phase classification by the classifier ML model with description of the test results within each phase, in accordance with some embodiments of the present invention.

Reference is now made to FIG. 12, which is a confusion matrix for CT abdomen with contrast phase classification by the classifier ML model with description of the test results within each phase, in accordance with some embodiments of the present invention. Results for the results of the classifier ML model are compared to the ground truth. The diagonal cells 1202 indicate the correct predictions by the classifier ML model including phase prediction accuracy and the number of correct predictions. Data in parentheses are 95% confidence intervals.

Figure 13:
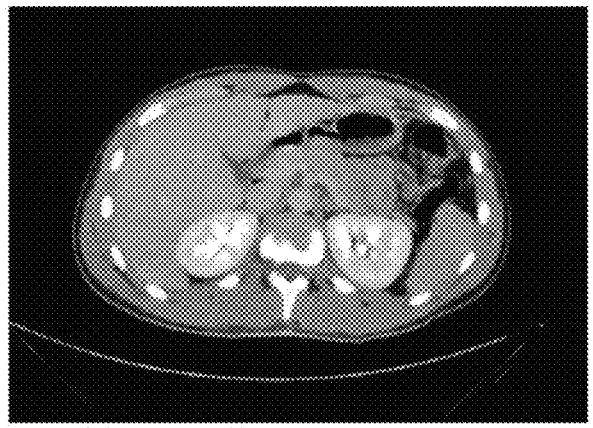
FIG. 13 provides some examples of abdominal CT scans misclassified by the classifier ML model, during the experiment, in accordance with some embodiments of the present invention.
Figure 13:
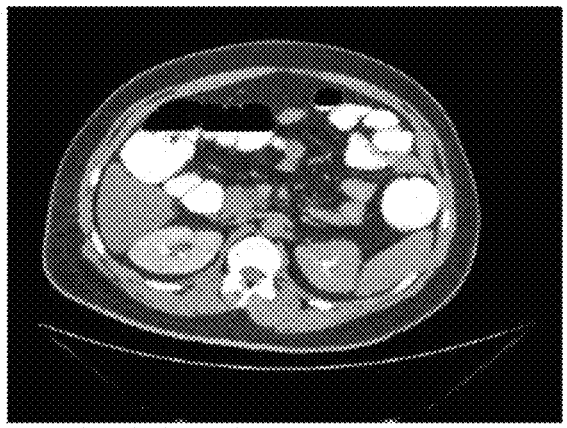
Figure 13:
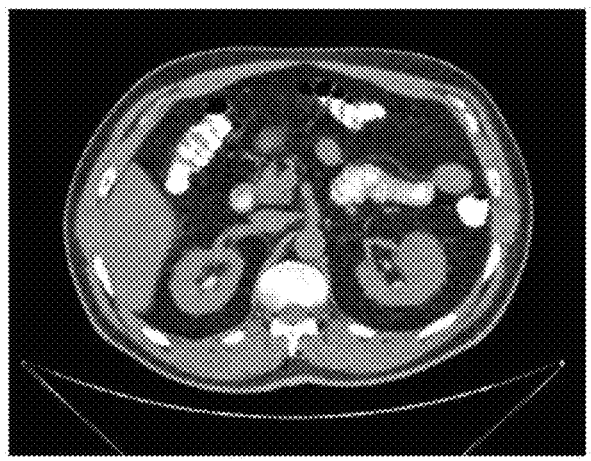
Figure 13:
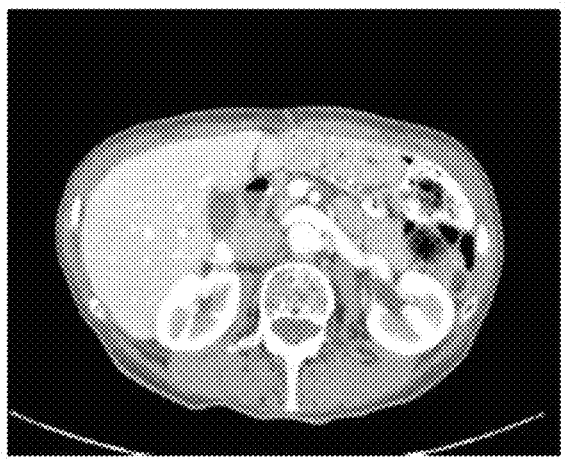

Reference is now made to FIG. 13, which provides some examples of abdominal CT scans misclassified by the classifier ML model, during the experiment, in accordance with some embodiments of the present invention. Typically, the misclassification occurred when a scan might be in between phases, indicating that the misclassification may not necessarily be a full error, but may be partially true. The misclassification in between phases may be due to improper timing of capture of the CT scan itself, when the CT scan was taken in between phases rather than during a target phase. When the regressor ML model is used, the misclassification may be learned as a new contrast phase using the zero-shot learning approach described herein. New contrast phases may be created to represent the misclassification category, enabling the classifier ML model to learn the new category, and correctly label new CT scans in between phases into the new category.

Zero-Shot Learning for Abdominal CT Phases

To investigate the potential of the zero-shot learning approach, 30 scans falling into the nephrogenic phase time range were randomly sampled and labelled by an expert radiologist to measure precision. 60% (18 out of 30) of the samples were identified correctly by the regression ML model.

Transfer Learning from Abdominal Scans to Chest CT

Reference is now made to FIG. 14, which is a table presenting transfer learning results, for the experiment, in accordance with some embodiments of the present invention. An ML model trained using transfer learning for CT chest contrast enhancement from an ML model trained for abdomen CT scans results in improved performance compared to training from scratch, most significantly for a small training set. Applying the trained abdominal contrast enhancement phase classifier on the chest CT test set resulted in an AUC 0.776 (95% CI: 0.721, 0.832) vs. random baseline 0.453 (95% CI: 0.382, 0.524). Transfer learning using 100 samples of chest CT, results in an AUC of 0.999 (95% CI: 0.998, 1.000) compared to 0.752 (95% CI: 0.694, 0.810) when trained from scratch. Data in parentheses are 95% confidence intervals.

DISCUSSION

Abdomen Contrast Phases Classification.

The reported results show that a fully automated approach using an ML model for contrast enhancement phase identification on abdomen CT can be trained using (optionally only) weak labels extracted from DICOM metadata, achieving strong performance. Using ResNet18 (e.g., as described with reference to "He") as a benchmark, different ML models and input configurations were evaluated. It was discovered that the 12-layer CNN with a volumetric input resulted in the best performance when measured against radiologist labels, with 93.3% test accuracy (166 of 178; 95% CI: 89.3%, 96.6%). Inventors hypothesize that the advantage of using a volumetric input is that the volumetric input provides contextual information that is not available for a single slice input, while preserving some information that would be lost using projections.

Most misclassifications occur between contiguous phases, where there is likely to be some overlapping clinical features.

Figure 15:
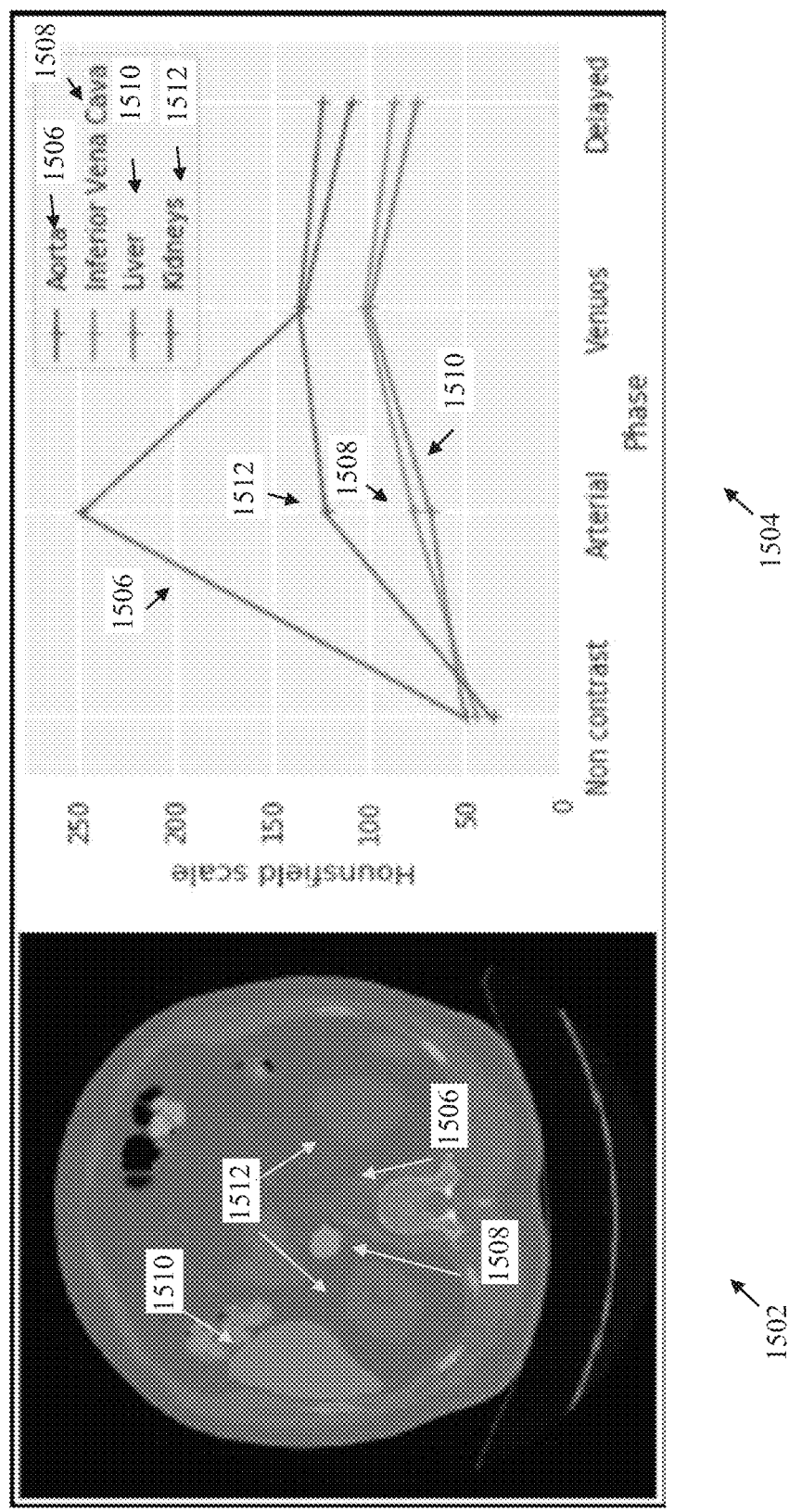
FIG. 15 is a schematic depicting overlap of clinical indicators associated with different phases demonstrated by a quantitative analysis, for the experiment, in accordance with some embodiments of the present invention.

Reference is now made to FIG. 15, which is a schematic depicting overlap of clinical indicators associated with different phases demonstrated by a quantitative analysis, for the experiment, in accordance with some embodiments of the present invention. An example abdominal CT axial slice 1502, and a graph 1504 of Hounsfield units as a function of contrast phases for different organs (aorta 1506, inferior vena cava 1508, liver 1510, and kidneys 1512) depicted in CT slice 1502 is presented. Measurements were taken using an automated segmentation algorithm on 800 different cases.

For scans in the arterial phase, the classifier ML model had an accuracy of 87.9% (29 of 33; 95% CI: 75.7%, 12.1%), with all other cases incorrectly classified as being in the contiguous portal venous phase. This is also highlighted by the high top-2 accuracies, indicating that the ground truth is in most cases the second most likely prediction of the ML model. It is noted that the reliance on information contained in the DICOM headers, restricts the classifier ML model to the phases represented in the DICOM metadata. However, the proposed Zero-Shot learning approach to phase identification based on the regressor ML model, improves upon the classifier ML model, by utilizes the existing phases to generalize to clinical phases not represented in the training dataset, which may also serve as a possible mitigation.

Zero-Shot Learning for Abdominal CT Phases.

Figure 16:
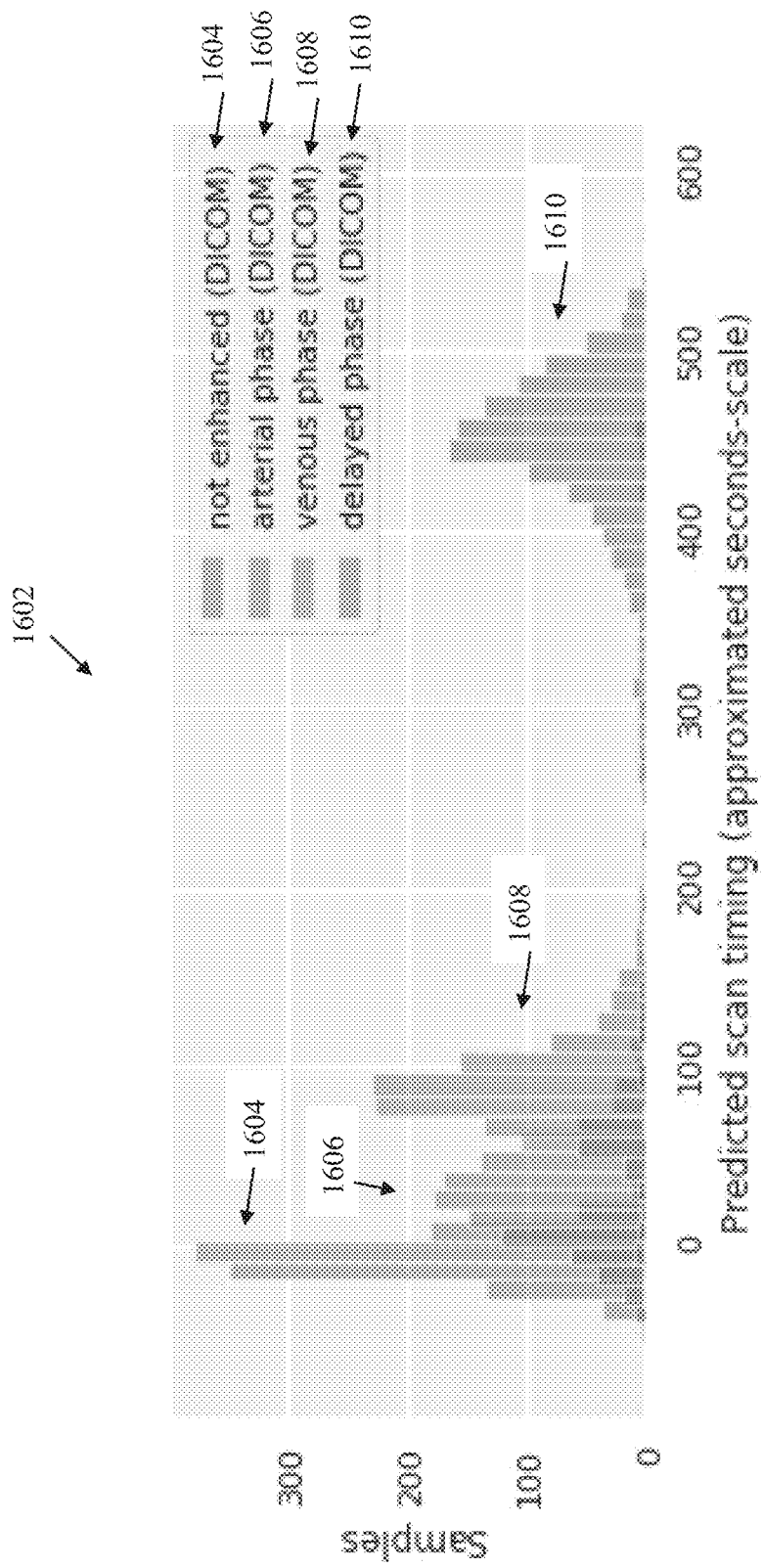
FIG. 16 is a graph presenting the distribution of predicted delays in seconds for the validation set, obtained from the regression ML model trained to predict scanning delay following IV contrast administration, for the experiment, in accordance with some embodiments of the present invention.

Reference is now made to FIG. 16, which is a graph 1602 presenting the distribution of predicted delays in seconds for the validation set, obtained from the regression ML model trained to predict scanning delay following IV contrast administration, for the experiment, in accordance with some embodiments of the present invention. Graph 1602 presents the predicted scan timing versus a number of samples, for the DICOM categories of not enhanced 1604, arterial phase 1606, venous phase 1608, and delayed phase 1610.

Figure 17:
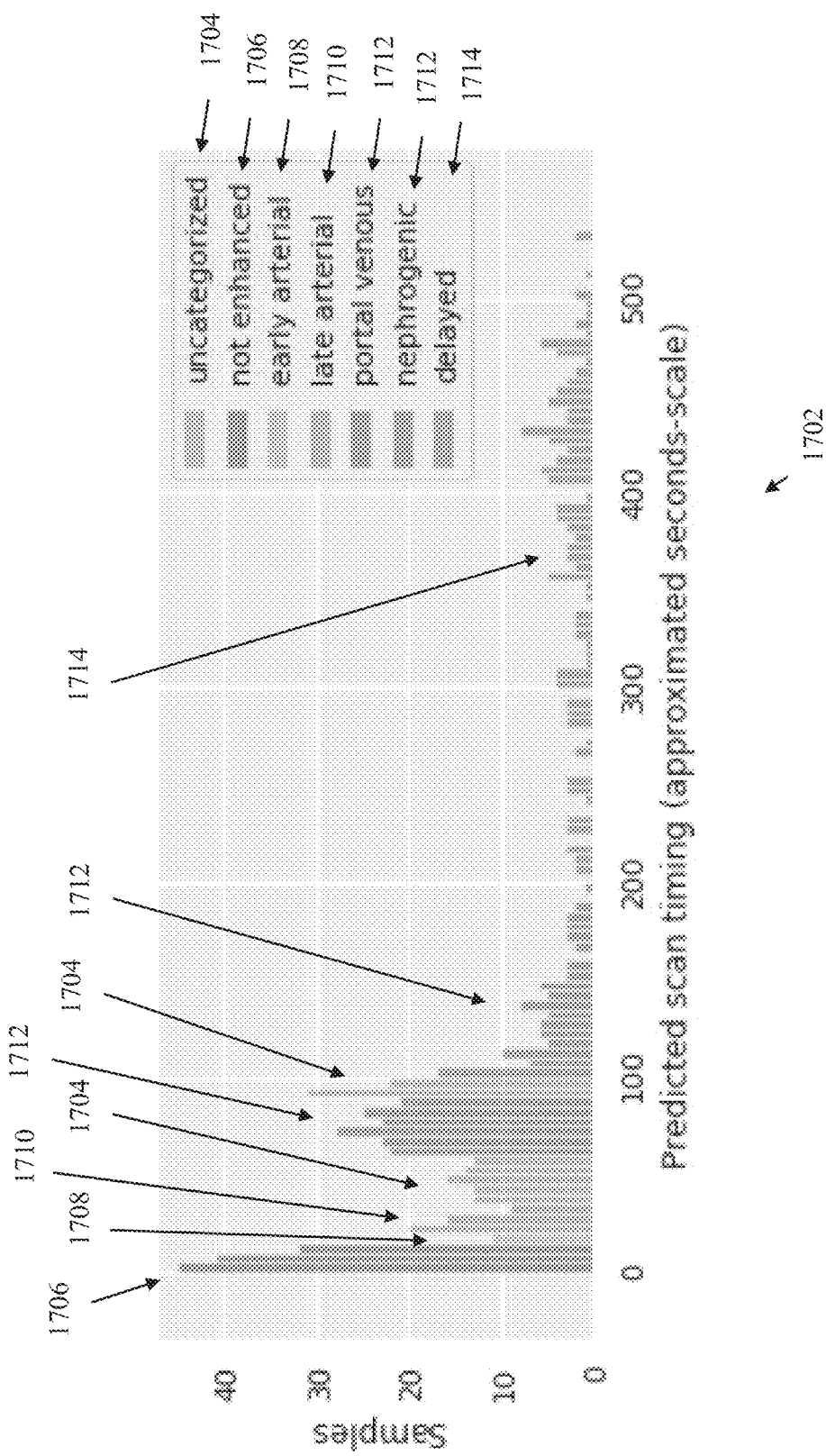
FIG. 17 is a graph presenting the distribution of predicted delays in seconds for a new held out dataset including 1000 random, unlabeled samples, for the experiment, in accordance with some embodiments of the present invention.

Reference is now made to FIG. 17, which is a graph 1702 presenting the distribution of predicted delays in seconds for a new held out dataset including 1000 random, unlabeled samples, for the experiment, in accordance with some embodiments of the present invention. The predicted scanning delays take on a range of values up to 600 seconds. Using the predicted scanning delay and time ranges defined for each phase as shown in the table of FIG. 10, Inventors attempt to categorize the contrast phase in finer temporal granularity than the initial 4 labels defined by DICOM (e.g., as in graph 1602). As illustrated in graph 1702, the distribution of predicted demonstrate four defined peaks within the first 100 seconds indicative of the non-contrast interval 1706, early 1708 and late 1710 arterial phases and portal venous 1712 phases. A long subsequent tail spanning between 100 seconds and 600 seconds may be visually divided into an earlier nephrogenic phase 1712 and later delayed excretory phase 1714. Inventors found that 60% of the samples were identified correctly, with 30% in portal venous or delayed phases. The regression ML model shows that fine-grained information may be extracted from aggregated noisy labels.

Transfer Learning from Abdominal Scans to Chest CT.

The potential of transfer learning between the network trained on CT abdomen to CT chest studies was next explored. Through an analysis based on gradient saliency maps and an automated segmentation algorithm, Inventors found that indicators in aorta were used by the classifier ML model to classify contrast phase in the abdomen.

Figure 18:
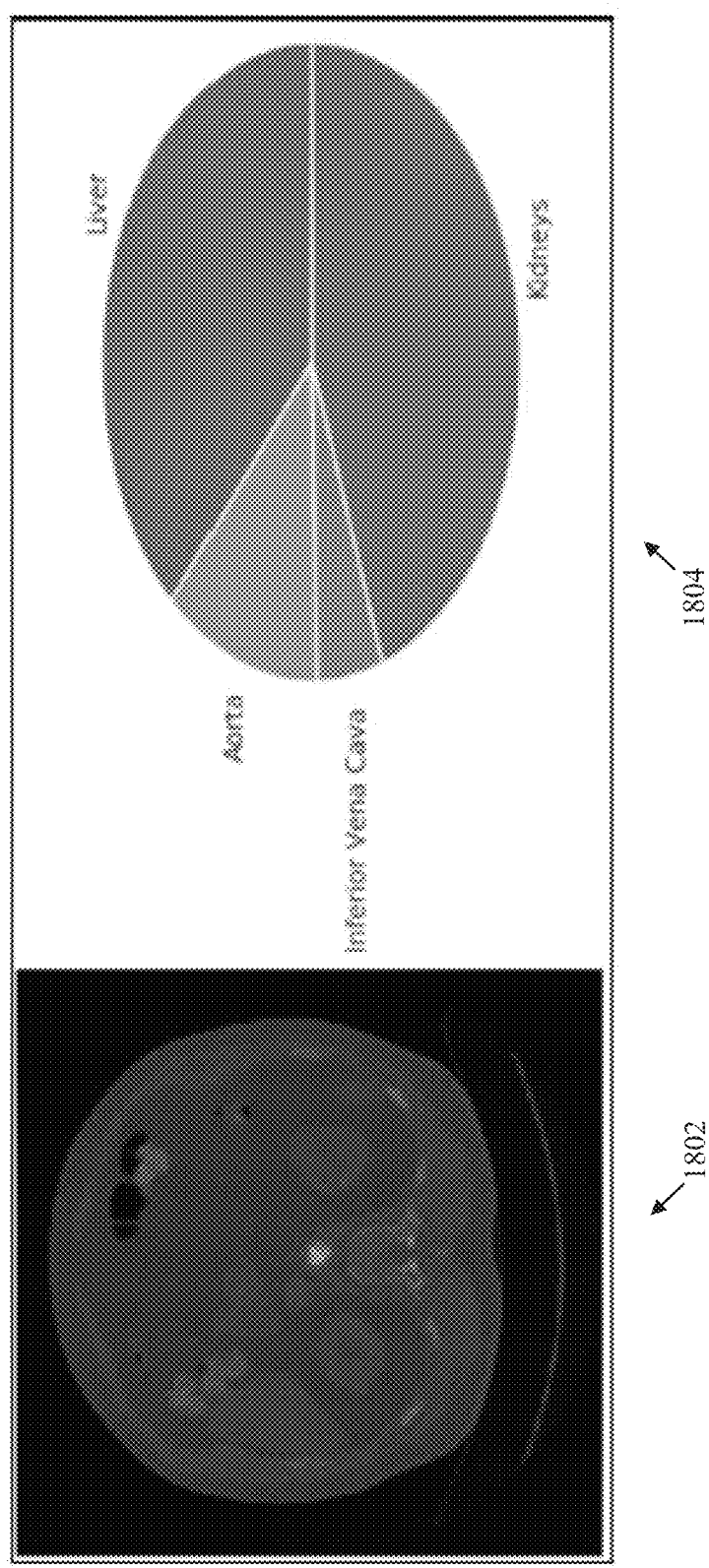
FIG. 18, which is a schematic depicting a gradient saliency map of an axial CT abdomen slice in the arterial phase, and a pie chart depicting average intersection of gradients and segmentation mask for each organ (aorta, liver, kidneys, inferior vena cava) for 100 scans, for the experiment, in accordance with some embodiments of the present invention.

Reference is now made to FIG. 18, which is a schematic depicting a gradient saliency map of an axial CT abdomen slice in the arterial phase 1802, and a pie chart 1804 depicting average intersection of gradients and segmentation mask for each organ (aorta, liver, kidneys, inferior vena cava) for 100 scans, for the experiment, in accordance with some embodiments of the present invention.

Figure 19:
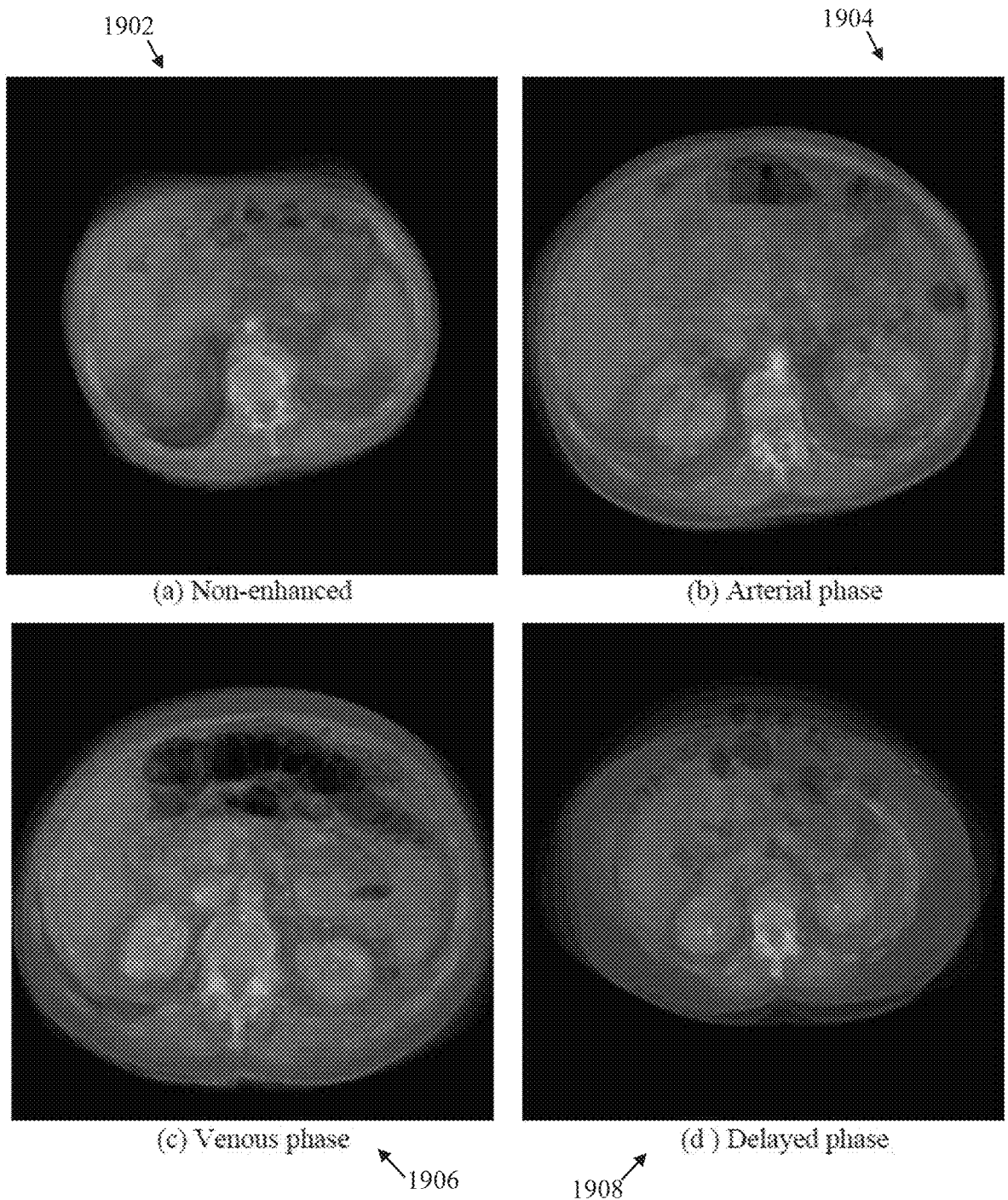
FIG. 19 is a schematic depicting gradient saliency maps for abdomen contrast phase classifier ML model, for the experiment, in accordance with some embodiments of the present invention.

Reference is now made to FIG. 19, which is a schematic depicting gradient saliency maps for abdomen contrast phase classifier ML model, for the experiment, in accordance with some embodiments of the present invention. Gradient saliency maps are shown for the non-enhanced 1902, arterial phase 1904, venous phase 1906, and delayed phase 1908 contrast phases. Features used by the classifier ML model generally align with commonly-used clinical indicators.

Given that enhancement of the aorta is common indicator of contrast enhancement in both the abdomen and chest, this highlights the potential of a transfer learning approach. The out-of-box abdomen model performs noticeably better than a random model in predicting chest enhancement, with an AUC of 0.776 (95% CI: 0.721, 0.832) compared to 0.453 (95% CI: 0.382, 0.524), verifying the relatedness of these tasks. Inventors also discovered that by using only 100 samples of chest CT, transfer learning from abdomen results in an AUC of 0.999 (95% CI: 0.998, 1.000) which is a significant improvement over training from scratch, for which an AUC of only 0.752 (95% CI: 0.694, 0.810) is achieved. This demonstrates the potential value of biomedical understanding in making optimal use of available datasets in developing an ML model. However, since identification of contrast enhancement in the chest is known to be based on similar clinical indicators to the abdomen, this approach might not extend to different tasks or body parts where the relationship is not clear, but this approach might extend to different tasks and/or body parts where the relationship is more clear.

Transfer Learning from Abdominal Scans to Chest CT.

The potential of transfer learning between the network trained on CT abdomen to CT chest studies was next explored. Through an analysis based on gradient saliency maps and an automated segmentation algorithm, indicators in aorta were found to be used by the model to classify contrast phase in the abdomen. Given that enhancement of the aorta is common indicator of contrast enhancement in both the abdomen and chest, this highlights the potential of a transfer learning approach. The out-of-box abdomen model performs noticeably better than a random model in predicting chest enhancement, with an AUC of 0.776 (95% CI: 0.721, 0.832) compared to 0.453 (95% CI: 0.382, 0.524), verifying the relatedness of these tasks. Inventors also discovered that by using only 100 samples of chest CT, transfer learning from abdomen results in an AUC of 0.999 (95% CI: 0.998, 1.000) which is a significant improvement over training from scratch, for which an AUC of only 0.752 (95% CI: 0.694, 0.810) is achieved. This demonstrates the potential value of biomedical understanding in making optimal use of available datasets in developing an algorithm. Since identification of contrast enhancement in the chest is known to be based on similar clinical indicators to the abdomen, this approach might not extend to different tasks or body parts where the relationship is not clear.

CONCLUSION

In this experiment, Inventors apply ML models to achieve highly accurate automatic categorization of four standard IV contrast phase in Abdominal CT studies. Reframing the classifier ML model into a regression ML model, aimed at predicting the seconds from IV contrast administration, resulted in finer resolution including non-contrast, early and late arterial, portal, nephrogenic and delayed venous phases. Inventors demonstrated through transfer learning within the body that the learned features can extend to successfully predict contrast phases in chest CT.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant machine learning models will be developed and the scope of the term machine learning model is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer-implemented method of training a machine learning (ML) model for classification of contrast phases of a target medical image, comprising:
    accessing a plurality of medical images of a plurality of subjects, depicting a plurality of contrast phases of contrast administered to the respective subject;
    accessing for a first subset of the plurality of medical images, metadata indicating a respective contrast phase selected from the plurality of contrast phases, wherein a second subset of the plurality of medical images are unassociated with metadata;
    mapping each respective contrast phase of the plurality of contrast phases to a respective time interval indicating estimated amount of time from a start of contrast administration to time of capture of the respective medical image;
    creating a training dataset, by labelling images of the first subset with a label indicating the respective time interval, and including the second subset as non-labelled images; and
    training the ML model using the training dataset for generating an outcome of a target time interval indicating estimated amount of time from the start of contrast administration, in response to an input of a target medical image.

2. The computer-implemented method of claim 1, further comprising:
    accessing a second plurality of medical images of a second plurality of subjects, depicting the plurality of contrast phases and unassociated with metadata indicating respective contrast phases;
    feeding each one of the second plurality of medical images into the ML model;
    obtaining as the outcome of the ML model, a plurality of target time intervals for the second plurality of medical images;
    clustering the plurality of target time intervals for the second plurality of medical images into a plurality of clusters;
    mapping a first subset of the plurality of clusters to the plurality of contrast phases, wherein a second subset of the plurality of clusters is non-mapped to the plurality of contrast phases; and
    at least one of: (i) designating at least one new contrast phase for the second subset of the plurality of clusters, and (ii) designating a plurality of new contrast phases to replace a certain contrast phase of the plurality of contrast phases for the first subset of the plurality of clusters.

3. The computer-implemented method of claim 2, wherein the plurality of contrast phases are selected from a group consisting of: not enhanced, arterial phase, venous phase, and delayed phase, wherein the at least one new contrast phase comprises a nephrogenic phase between the venous phase and delayed phase, and wherein the designating the plurality of new contrast phases to replace the certain contrast phase comprise early arterial and late arterial replacing arterial phase.

4. The computer-implemented method of claim 2, further comprising mapping the target time interval to one of a plurality of contrast phases including the at least one new contrast phase, and the designated plurality of new contrast phases, and automatically generating a tag indicating the mapped one of the plurality of contrast phases for the target image.

5. The computer-implemented method of claim 4, wherein mapping comprises mapping a target time interval of zero to all phases before injection, mapping the target time interval of 15-20 seconds to early arterial contrast phase, mapping the target time interval of 20-35 seconds to later arterial contrast phase, mapping the target time interval of 60-90 seconds to hepatic portal venous contrast phase, mapping the target time interval of 100-200 seconds to nephrogenic contrast phase, and mapping the target time interval of 6-10 minutes to delayed contrast phase.

6. The computer-implemented method of claim 1, wherein the training dataset comprises a second training dataset, and training the ML model comprises training the second ML model, and further comprising:
    creating a first training dataset, by labelling images of the first subset with a label indicating the respective contrast phase, and including the second subset as non-labelled images;
    training a first ML model using the first training dataset for generating a certain classification label indicating a certain contrast phase selected from a plurality of classification labels indicating the plurality of contrast phases; and
    training the second ML model on the second training dataset by using the first ML model as an initial state.

7. The computer-implemented method of claim 6, wherein the metadata is used as weak labels for the first training dataset, and training the first ML model is done using semi-supervised classification training.

8. The computer-implemented method of claim 6, wherein the first ML model comprises a classifier, and the second ML model comprises a regressor.

9. The computer-implemented method of claim 6, wherein the first ML model and the second ML model are implemented using a common convolutional neural network (CNN) architecture, wherein the first ML model comprises an output layer with a plurality of outputs corresponding to the plurality of contrast phases and the second ML model comprises an output layer with a single output corresponding to the target time interval, wherein weights of the second ML model prior to training are initialized with weights of the trained first ML model.

10. The computer-implemented method of claim 1, wherein the ML model comprises a first ML model trained on medical images depicting a first body region, and further comprising creating a second training dataset using second medical images depicting a second body region, and training a second ML model on the second training dataset using the trained first ML model as an initial state, wherein the first ML model and the second ML model share a common feature space with similarities in distribution of features associated with contrast enhancement in images depicting the first body region and images depicting the second body region.

11. The computer-implemented method of claim 10, wherein the second training dataset includes less than about 100 medical images, and the first training dataset includes over about 10000 medical images.

12. The computer-implemented method of claim 10, wherein the first ML model is trained on CT abdomen medical images, and the second ML model is trained on CT chest medical images, or the first ML model is trained on CT chest medical images, and the second ML model is trained on CT abdomen medical images.

13. The computer-implemented method of claim 1, wherein the metadata comprises DICOM free text stored as metadata.

14. The computer-implemented method of claim 1, wherein each of the plurality of medical images comprises a three (3D) dataset, and further comprising extract an input representation of the 3D dataset, wherein the training dataset includes the input representation, and a target input representation of the target medical image is fed into the trained ML model.

15. The computer-implemented method of claim 14, wherein the input representation is selected from a group consisting of: a single two dimensional (2D) slice selected from a plurality of slices of the 3D dataset, a maximum intensity projection (MIP) in a selected plane computed from the 3D dataset, and a volumetric subset selected from the 3D dataset.

16. The computer-implemented method of claim 1, wherein the ML model is implemented as a convolutional neural network (CNN) with 12 convolutional layers, each layer with a filter size 3×3 and stride 1, wherein after every 2 convolutions, downsampling by max-pooling is performed with kernel size 2×2 and stride 2, where the first 2 convolutional layers have 16 filters, with the number of filters doubled after each downsampling layer except for the last 2 convolutional layers, which each include 256 filters, wherein a global max-pooling layer is applied to the final feature maps and output to single output node, and wherein batch normalization (BN) is applied after each convolution before rectified linear unit activation (ReLU).

17. The computer-implemented method of claim 1, wherein mapping comprises: mapping a non-enhanced contrast phase to a value of zero seconds, mapping an arterial contrast phase to a value of 27.5 seconds, mapping a venous contrast phase to a value of 75 seconds, and mapping a delayed contrast phase to a value of 480 seconds.

18. The computer-implemented method of claim 1, wherein the plurality of medical images and the target medical image comprise a CT scan, and the plurality of contrast phases are based on intravenous (IV) contrast administered to the respective subject.

19. A computer-implemented method of automatically tagging a target medical image with an indication of a contrast phase, comprising:
inputting a target medical image into an ML model trained on a training dataset of a plurality of medical images of a plurality of subjects, depicting a plurality of contrast phases of contrast administered to the respective subject, wherein a first subset of medical images having metadata indicating a respective contrast phase selected from the plurality of contrast phases are labelled with a time interval indicating estimated amount of time from a start of contrast administration mapped to the respective contrast phase, and a second subset of the plurality of medical images unassociated with metadata are unlabeled;
obtaining from the ML model, an outcome of a target time interval indicating estimated amount of time from the start of contrast administration; and
automatically tagging the target medical image with a tag indicating the target time interval.

20. A device for training a machine learning (ML) model for classification of contrast phases of a target medical image, comprising:
at least one hardware processor executing a code for:
accessing a plurality of medical images of a plurality of subjects, depicting a plurality of contrast phases of contrast administered to the respective subject;
accessing for a first subset of the plurality of medical images, metadata indicating a respective contrast phase selected from the plurality of contrast phases, wherein a second subset of the plurality of medical images are unassociated with metadata;
mapping each respective contrast phase of the plurality of contrast phases to a respective time interval indicating estimated amount of time from a start of contrast administration to time of capture of the respective medical image;
creating a training dataset, by labelling images of the first subset with a label indicating the respective time interval, and including the second subset as non-labelled images; and
training the ML model using the training dataset for generating an outcome of a target time interval indicating estimated amount of time from the start of contrast administration, in response to an input of a target medical image.

* * * * *